US007226990B2

(12) United States Patent
Knudsen et al.

(10) Patent No.: US 7,226,990 B2
(45) Date of Patent: Jun. 5, 2007

(54) EXTENDIN DERIVATIVES

(75) Inventors: Liselotte Bjerre Knudsen, Valby (DK); Per Olaf Huusfeldt, Copenhagen K (DK); Per Franklin Nielsen, Værlose (DK); Kjeld Madsen, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 302 days.

(21) Appl. No.: 09/886,311

(22) Filed: Jun. 21, 2001

(65) Prior Publication Data

US 2001/0047084 A1  Nov. 29, 2001

Related U.S. Application Data

(63) Continuation of application No. 09/312,177, filed on May 14, 1999, now abandoned, which is a continuation of application No. PCT/DK99/00086, filed on Feb. 24, 1999.

(60) Provisional application No. 60/084,351, filed on May 5, 1998.

(30) Foreign Application Priority Data

Feb. 27, 1998  (DE)  ................................. 0274/98

(51) Int. Cl.
*A61K 38/28* (2006.01)
*A61K 38/00* (2006.01)
*C07K 16/00* (2006.01)

(52) U.S. Cl. .................. 530/308; 530/300; 530/303; 530/322; 530/324; 530/345; 530/399; 530/402; 514/2; 514/3; 514/12; 514/23; 514/866

(58) Field of Classification Search ................ 530/308, 530/300, 303, 322, 324, 345, 399, 402; 514/2, 514/3, 12, 23, 866
See application file for complete search history.

(56) References Cited

U.S. PATENT DOCUMENTS

| 5,424,286 | A  | * | 6/1995  | Eng ............................... 514/2 |
| 5,545,618 | A  |   | 8/1996  | Buckley et al. ............... 514/12 |
| 5,614,492 | A  |   | 3/1997  | Habener ...................... 514/12 |
| 5,631,224 | A  |   | 5/1997  | Efendic et al. ............... 514/12 |
| 6,268,343 | B1 |   | 7/2001  | Knudsen et al. .............. 514/12 |
| 6,458,924 | B2 |   | 10/2002 | Knudsen et al. ............ 530/324 |

FOREIGN PATENT DOCUMENTS

| WO | WO 87/06941 |   | 11/1987 |
| WO | WO 90/11296 |   | 10/1990 |
| WO | WO 94/26778 |   | 11/1994 |
| WO | WO 96/29342 | * | 9/1996 |
| WO | WO 97/46584 |   | 12/1997 |
| WO | WO 9805351 A1 | * | 2/1998 |
| WO | WO 98/08871 |   | 3/1998 |

OTHER PUBLICATIONS

Bowie et al., Science, vol. 247, pp. 1306-1310, 1990.*
Houghten et al., Vaccines 86, Cold Spring Harbor Laboratory, pp. 21-25, 1986.*

* cited by examiner

*Primary Examiner*—Jon Weber
*Assistant Examiner*—Abdel A. Mohamed
(74) *Attorney, Agent, or Firm*—Richard W. Bork; Reza Green

(57) ABSTRACT

The present invention relates to novel derivatives of exendin-4 or exendin-4 fragments, wherein the derivatives have a lipophilic substituent attached, optionally via a spacer, to an amino acid residue, which is not the N-terminal or C-terminal amino acid residue of the derivative.

10 Claims, No Drawings

SEQUENCE LISTING

<160> NUMBER OF SEQ ID NOS: 3

<210> SEQ ID NO 1
<211> LENGTH: 31
<212> TYPE: PRT
<213> ORGANISM: Artificial Sequence
<220> FEATURE:
<223> OTHER INFORMATION: Variation; Xaa at position 31 is any amino acid

<400> SEQUENCE: 1

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa
            20                  25                  30

<210> SEQ ID NO 2
<211> LENGTH: 40
<212> TYPE: PRT
<213> ORGANISM: Artificial Sequence
<220> FEATURE:
<223> OTHER INFORMATION: Variation; Xaa at position 2 is Ser or Gly;
<220> FEATURE:
<223> OTHER INFORMATION: Xaa at position 3 is Asp or Glu

<400> SEQUENCE: 2

His Xaa Xaa Gly Thr Phe Ile Thr Ser Asp Leu Ser Lys Gln Met Glu
 1               5                  10                  15

Glu Glu Ala Val Arg Leu Phe Ile Glu Trp Leu Lys Asn Gly Gly Pro
            20                  25                  30

```
Ser Ser Gly Ala Pro Pro Ser
        35              40

<210> SEQ ID NO 3
<211> LENGTH: 31
<212> TYPE: PRT
<213> ORGANISM: Artificial Sequence
<220> FEATURE:
<223> OTHER INFORMATION: Variation

<400> SEQUENCE: 3

Asp Leu Ser Lys Gln Met Glu Glu Glu Ala Val Arg Leu Phe Ile Glu
 1               5                  10                  15

Trp Leu Lys Asn Gly Gly Pro Ser Ser Gly Ala Pro Pro Pro Ser
            20                  25                  30
```

EXTENDIN DERIVATIVES

CROSS REFERENCE TO RELATED APPLICATIONS

This application is a continuation of U.S. Ser. No. 09/312,177 filed 14 May 1999, now abandoned, which is a continuation of PCT/DK99/00086 filed Feb. 24, 1999 and claims priority under 35 U.S.C. 119 of Danish application 0274/98 filed Feb. 27, 1998, and U.S. provisional application 60/084,357 filed May 5, 1998, the contents of which are fully incorporated herein by reference.

FIELD OF THE INVENTION

The present invention relates to novel derivatives of human glucagon-like peptide-1 (GLP-1) and fragments thereof and analogues of such fragments which have a protracted profile of action and to methods of making and using them. The invention furthermore relates to novel derivatives of exendin and the uses of such derivatives.

BACKGROUND OF THE INVENTION

Peptides are widely used in medical practice, and since they can be produced by recombinant DNA technology it can be expected that their importance will increase also in the years to come. When native peptides or analogues thereof are used in therapy it is generally found that they have a high clearance. A high clearance of a therapeutic agent is inconvenient in cases where it is desired to maintain a high blood level thereof over a prolonged period of time since repeated administrations will then be necessary. Examples of peptides which have a high clearance are: ACTH, corticotropin-releasing factor, angiotensin, calcitonin, insulin, glucagon, glucagon-like peptide-1, glucagon-like peptide-2, insulin-like growth factor-1, insulin-like growth factor-2, gastric inhibitory peptide, growth hormone-releasing factor, pituitary adenylate cyclase activating peptides, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, superoxide dismutase, interferon, asparaginase, arginase, arginine deaminase, adenosine deaminase and ribonuclease. In some cases it is possible to influence the release profile of peptides by applying suitable pharmaceutical compositions, but this approach has various shortcomings and is not generally applicable.

The hormones regulating insulin secretion belong to the so-called enteroinsular axis, designating a group of hormones, released from the gastrointestinal mucosa in response to the presence and absorption of nutrients in the gut, which promote an early and potentiated release of insulin. The enhancing effect on insulin secretion, the so-called incretin effect, is probably essential for a normal glucose tolerance. Many of the gastrointestinal hormones, including gastrin and secretin (cholecystokinin is not insulinotropic in man), are insulinotropic, but the only physiologically important ones, those that are responsible for the incretin effect, are the glucose-dependent insulinotropic polypeptide, GIP, and glucagon-like peptide-1 (GLP-1). Because of its insulinotropic effect, GIP, isolated in 1973 (1) immediately attracted considerable interest among diabetologists. However, numerous investigations carried out during the following years clearly indicated that a defective secretion of GIP was not involved in the pathogenesis of insulin dependent diabetes mellitus (IDDM) or non insulin-dependent diabetes mellitus (NIDDM) (2). Furthermore, as an insulinotropic hormone, GIP was found to be almost ineffective in NIDDM (2). The other incretin hormone, GLP-1 is the most potent insulinotropic substance known (3). Unlike GIP, it is surprisingly effective in stimulating insulin secretion in NIDDM patients. In addition, and in contrast to the other insulinotropic hormones (perhaps with the exception of secretin) it also potently inhibits glucagon secretion. Because of these actions it has pronounced blood glucose lowering effects particularly in patients with NIDDM.

GLP-1, a product of the proglucagon (4), is one of the youngest members of the secretin-VIP family of peptides, but is already established as an important gut hormone with regulatory function in glucose metabolism and gastrointestinal secretion and metabolism (5). The glucagon gene is processed differently in the pancreas and in the intestine. In the pancreas (9), the processing leads to the formation and parallel secretion of 1) glucagon itself, occupying positions 33–61 of proglucagon (PG); 2) an N-terminal peptide of 30 amino acids (PG (1–30)) often called glicentin-related pancreatic peptide, GRPP (10, 11); 3) a hexapeptide corresponding to PG (64–69); 4) and, finally, the so-called major proglucagon fragment (PG (72–158)), in which the two glucagon-like sequences are buried (9). Glucagon seems to be the only biologically active product. In contrast, in the intestinal mucosa, it is glucagon that is buried in a larger molecule, while the two glucagon-like peptides are formed separately (8). The following products are formed and secreted in parallel: 1) glicentin, corresponding to PG (1–69), with the glucagon sequence occupying residues Nos. 33–61 (12); 2) GLP-1(7–36)amide (PG (78–107))amide (13), not as originally believed PG (72–107)amide or 108, which is inactive). Small amounts of C-terminally glycine-extended but equally bioactive GLP-1(7–37), (PG (78–108)) are also formed (14); 3) intervening peptide-2 (PG (111–122)amide) (15); and 4)GLP-2 (PG (126–158)) (15, 16). A fraction of glicentin is cleaved further into GRPP (PG (1–30)) and oxyntomodulin (PG (33–69)) (17, 18). Of these peptides, GLP-1, has the most conspicuous biological activities.

Being secreted in parallel with glicentin/enteroglucagon, it follows that the many studies of enteroglucagon secretion (6, 7) to some extent also apply to GLP-1 secretion, but GLP-1 is metabolised more quickly with a plasma half-life in humans of 2 min (19). Carbohydrate or fat-rich meals stimulate secretion (20), presumably as a result of direct interaction of yet unabsorbed nutrients with the microvilli of the open-type L-cells of the gut mucosa. Endocrine or neural mechanisms promoting GLP-1 secretion may exist but have not yet been demonstrated in humans.

The incretin function of GLP-1(29–31) has been clearly illustrated in experiments with the GLP-1 receptor antagonist, exendin 9–39, which dramatically reduces the incretin effect elicited by oral glucose in rats (21, 22). The hormone interacts directly with the β-cells via the GLP-1 receptor (23) which belongs to the glucagon/VIP/calcitonin family of G-protein-coupled 7-transmembrane spanning receptors. The importance of the GLP-1 receptor in regulating insulin secretion was illustrated in recent experiments in which a targeted disruption of the GLP-1 receptor gene was carried out in mice. Animals homozygous for the disruption had greatly deteriorated glucose tolerance and fasting hyperglycaemia, and even heterozygous animals were glucose intolerant (24). The signal transduction mechanism (25) primarily involves activation of adenylate cyclase, but elevations of intracellular $Ca^{2+}$ are also essential (25, 26). The action of the hormone is best described as a potentiation of glucose stimulated insulin release (25), but the mechanism that couples glucose and GLP-1 stimulation is not known. It may involve a calcium-induced calcium release (26, 27). As already mentioned, the insulinotropic action of GLP-1 is preserved in diabetic β-cells. The relation of the latter to its ability to convey "glucose competence" to isolated insulin-secreting cells (26, 28), which respond poorly to glucose or GLP-1 alone, but fully to a combination of the two, is also not known. Equally importantly, however, the hormone also potently inhibits glucagon secretion (29). The mechanism is not known, but seems to be paracrine, via neighbouring insulin or somatostatin cells (25). Also the glucagonostatic action is glucose-dependent, so that the inhibitory effect decreases as blood glucose decreases. Because of this dual effect, if the plasma GLP-1 concentrations increase either by increased secretion or by exogenous infusion the molar ratio of insulin to glucagon in the blood that reaches the liver via the portal circulation is greatly increased, whereby hepatic glucose production decreases (30). As a result blood glucose concentrations decrease. Because of the glucose dependency of the insulinotropic and glucagonostatic actions, the glucose lowering effect is self-limiting, and the hormone, therefore, does not cause hypoglycaemia regardless of dose (31). The effects are preserved in patients with diabetes mellitus (32), in whom infusions of slightly supraphysiological doses of GLP-1 may completely normalise blood glucose values in spite of poor metabolic control and secondary failure to sulphonylurea (33). The importance of the glucagonostatic effect is illustrated by the finding that GLP-1 also lowers blood glucose in type-1 diabetic patients without residual β-cell secretory capacity (34).

In addition to its effects on the pancreatic islets, GLP-1 has powerful actions on the gastrointestinal tract. Infused in physiological amounts, GLP-1 potently inhibits pentagastrin-induced as well as meal-induced gastric acid secretion (35, 36). It also inhibits gastric emptying rate and pancreatic enzyme secretion (36). Similar inhibitory effects on gastric and pancreatic secretion and motility may be elicited in humans upon perfusion of the ileum with carbohydrate- or lipid-containing solutions (37, 38). Concomitantly, GLP-1 secretion is greatly stimulated, and it has been speculated that GLP-1 may be at least partly responsible for this so-called "ileal-brake" effect (38). In fact, recent studies suggest that, physiologically, the ileal-brake effects of GLP-1 may be more important than its effects on the pancreatic islets. Thus, in dose response studies GLP-1 influences gastric emptying rate at infusion rates at least as low as those required to influence islet secretion (39).

GLP-1 seems to have an effect on food intake. Intraventricular administration of GLP-1 profoundly inhibits food intake in rats (40, 42). This effect seems to be highly specific. Thus, N-terminally extended GLP-1 (PG 72–107) amide is inactive and appropriate doses of the GLP-1 antagonist, exendin 9–39, abolish the effects of GLP-1 (41). Acute, peripheral administration of GLP-1 does not inhibit food intake acutely in rats (41, 42). However, it remains possible that GLP-1 secreted from the intestinal L-cells may also act as a satiety signal.

Not only the insulinotropic effects but also the effects of GLP-1 on the gastrointestinal tract are preserved in diabetic patients (43), and may help curtailing meal-induced glucose excursions, but, more importantly, may also influence food intake. Administered intravenously, continuously for one week, GLP-1 at 4 ng/kg/min has been demonstrated to dramatically improve glycaemic control in NIDDM patients without significant side effects (44). The peptide is fully active after subcutaneous administration (45), but is rapidly degraded mainly due to degradation by dipeptidyl peptidase IV-like enzymes (46, 47).

The amino acid sequence of GLP-1 is given i.a. by Schmidt et al. (*Diabetologia* 28 704–707 (1985). Although the interesting pharmacological properties of GLP-1(7–37) and analogues thereof have attracted much attention in recent years only little is known about the structure of these molecules. The secondary structure of GLP-1 in micelles has been described by Thornton et al. (*Biochemistry* 33 3532–3539 (1994)), but in normal solution, GLP-1 is considered a very flexible molecule. Surprisingly, we found that derivatisation of this relatively small and very flexible molecule resulted in compounds whose plasma profile were highly protracted and still had retained activity.

GLP-1 and analogues of GLP-1 and fragments thereof are potentially useful i.a. in the treatment of type 1 and type 2 diabetes. However, the high clearance limits the usefulness of these compounds, and thus there still is a need for improvements in this field. Accordingly, it is one object of the present invention to provide derivatives of GLP-1 and analogues thereof which have a protracted profile of action relative to GLP-1(7–37). It is a further object of the invention to provide derivatives of GLP-1 and analogues thereof which have a lower clearance than GLP-1(7–37). It is a further object of the invention to provide a pharmaceutical composition comprising a compound according to the invention and to use a compound of the invention to provide such a composition. Also, it is an object of the present invention to provide a method of treating insulin dependent and non-insulin dependent diabetes mellitus.

REFERENCES

1. Pederson R A. Gastric Inhibitory Polypeptide. In Walsh J H, Dockray G J (eds) Gut peptides: Biochemistry and Physiology, Raven Press, New York 1994, pp. 217259.
2. Krarup T. Immunoreactive gastric inhibitory polypeptide. Endocr Rev 1988; 9:122–134.
3. Ørskov C. Glucagon-like peptide-1, a new hormone of the enteroinsular axis. Diabetologia 1992; 35:701–711.
4. Bell G I, Sanchez-Pescador R, Laybourn P J, Najarian R C. Exon duplication and divergence in the human preproglucagon gene. Nature 1983; 304: 368–371.
5. Holst J J. Glucagon-like peptide-1 (GLP-1)—a newly discovered GI hormone. Gastroenterology 1994; 107: 1848–1855.
6. Holst J J. Gut glucagon, enteroglucagon, gut GLI, glicentin—current status. Gastroenterology 1983; 84:1602–1613.
7. Holst J J, Ørskov C. Glucagon and other proglucagon-derived peptides. In Walsh J H, Dockray G J, eds. Gut peptides: Biochemistry and Physiology. Raven Press, New York, pp. 305–340, 1993.
8. Ørskov C, Holst J J, Knuhtsen S, Baldissera F G A, Poulsen S S, Nielsen O V. Glucagon-like peptides GLP-1 and GLP-2, predicted products of the glucagon gene, are secreted separately from the pig small intestine, but not pancreas. Endocrinology 1986; 119:1467–1475.
9. Holst J J, Bersani M, Johnsen A H, Kofod H, Hartmann B, Ørskov C. Proglucagon processing in porcine and human pancreas. J Biol Chem, 1994; 269: 18827–1883.
10. Moody A J, Holst J J, Thim L, Jensen S L. Relationship of glicentin to proglucagon and glucagon in the porcine pancreas. Nature 1981; 289: 514–516.

11. Thim L, Moody A J, Purification and chemical characterisation of a glicentin-related pancreatic peptide (proglucagon fragment) from porcine pancreas. Biochim Biophys Acta 1982; 703:134–141.
12. Thim L, Moody A J. The primary structure of glicentin (Proglucagon). Regul Pept 1981; 2:139–151.
13. Ørskov C, Bersani M, Johnsen A H, Højrup P, Holst J J. Complete sequences of glucagon-like peptide-1 (GLP-1) from human and pig small intestine. J Biol. Chem. 1989; 264:12826–12829.
14. Ørskov C, Rabenhøj L, Kofod H, Wettergren A, Holst J J. Production and secretion of amidated and glycine-extended glucagon-like peptide-1 (GLP-1) in man. Diabetes 1991; 43: 535–539.
15. Buhl T, Thim L, Kofod H, Ørskov C, Harling H, & Holst J J: Naturally occurring products of proglucagon 111–160 in the porcine and human small intestine. J. Biol. Chem. 1988; 263:8621–8624.
16. Ørskov C, Buhl T, Rabenhøj L, Kofod H, Holst J J: Carboxypeptidase-B-like processing of the C-terminus of glucagon-like peptide-2 in pig and human small intestine. FEBS letters, 1989; 247:193–106.
17. Holst J J. Evidence that enteroglucagon (II) is identical with the C-terminal sequence (residues 33–69) of glicentin. Biochem J. 1980; 187:337–343.
18. Bataille D, Tatemoto K, Gespach C, Jörnvall H, Rosselin G, Mutt V. Isolation of glucagon-37 (bioactive enteroglucagon/oxyntomodulin) from porcine jejuno-ileum. Characterisation of the peptide. FEBS Lett 1982; 146:79–86.
19. Ørskov C, Wettergren A, Holst J J. The metabolic rate and the biological effects of GLP-1 7–36amide and GLP-1 7–37 in healthy volunteers are identical. Diabetes 1993; 42:658–661.
20. Elliott R M, Morgan L M, Tredger J A, Deacon S, Wright J, Marks V. Glucagon-like peptide-1 (7–36)amide and glucose-dependent insulinotropic polypeptide secretion in response to nutrient ingestion in man: acute post-prandial and 24-h secretion patterns. J Endocrinol 1993; 138: 159–166.
21. Kolligs F, Fehmann H C, Göke R, Göke B. Reduction of the incretin effect in rats by the glucagon-like peptide-1 receptor antagonist exendin (9–39)amide. Diabetes 1995; 44: 16–19.
22. Wang Z, Wang R M, Owji A A, Smith D M, Ghatei M, Bloom S R. Glucagon-like peptide-1 is a physiological incretin in rat. J. Clin. Invest. 1995; 95: 417–421.
23. Thorens B. Expression cloning of the pancreatic b cell receptor for the gluco-incretin hormone glucagon-like peptide 1. Proc Natl Acad Sci 1992; 89:8641–4645.
24. Scrocchi L, Auerbach A B, Joyner A L, Drucker D J. Diabetes in mice with targeted disruption of the GLP-1 receptor gene. Diabetes 1996; 45: 21A.
25. Fehmann H C, Göke R, Göke B. Cell and molecular biology of the incretin hormones glucagon-like peptide-1 (GLP-1) and glucose-dependent insulin releasing polypeptide (GIP). Endocrine Reviews, 1995; 16: 390–410.
26. Gromada J, Dissing S, Bokvist K, Renström E, Frøkjær-Jensen J, Wulff B S, Rorsman P. Glucagon-like peptide 1 increases cytoplasmic calcium in insulin-secreting btC3-cells by enhancement of intracellular calcium mobilisation. Diabetes 1995; 44: 767–774.
27. Holz G G, Leech C A, Habener J F. Activation of a cAMP-regulated $Ca^{2+}$signaling pathway in pancreatic β-cells by the insulinotropic hormone glucagon-like peptide-1. J Biol Chem. 1996; 270: 17749–17759.
28. Holz G G, Kühltreiber W M, Habener J F. Pancreatic beta-cells are rendered glucose competent by the insulinotropic hormone glucagon-like peptide-1(7–37). Nature 1993; 361:362–365.
29. Ørskov C, Holst J J, Nielsen O V: Effect of truncated glucagon-like peptide-1 (proglucagon 78–107 amide) on endocrine secretion from pig pancreas, antrum and stomach. Endocrinology 1988; 123:2009–2013.
30. Hvidberg A, Toft Nielsen M, Hilsted J, Ørskov C, Holst J J. Effect of glucagon-like peptide-1 (proglucagon 78–107amide) on hepatic glucose production in healthy man. Metabolism 1994; 43:104–108.
31. Qualmann C, Nauck M, Holst J J, Ørskov C, Creutzfeldt W. Insulinotropic actions of intravenous glucagon-like peptide-1 [7–36 amide] in the fasting state in healthy subjects. Acta Diabetologica, 1995; 32: 13–16.
32. Nauck M A, Heimesaat M M, Ørskov C, Holst J J, Ebert R, Creutzfeldt W. Preserved incretin activity of GLP-1 (7–36amide) but not of synthetic human GIP in patients with type 2-diabetes mellitus. J Clin Invest 1993; 91:301–307.
33. Nauck M A, Kleine N, Ørskov C, Holst J J, Willms B, Creutzfeldt W. Normalisation of fasting hyperglycaemia by exogenous GLP-1(7–36amide) in type 2-diabetic patients. Diabetologia 1993; 36:741–744.
34. Creutzfeldt W, Kleine N, Willms B, Ørskov C, Holst J J, Nauck M A. Glucagonostatic actions and reduction of fasting hyperglycaemia by exogenous glucagon-liem, peptide-1(7–36amide) in type I diabetic patients. Diabetes Care 1996; 19: 580–586.
35. Schjoldager B T G, Mortensen P E, Christiansen J, Ørskov C, Holst J J. GLP-1 (glucagon-like peptide-1) and truncated GLP-1, fragments of human proglucagon, inhibit gastric acid secretion in man. Dig. Dis. Sci. 1989; 35:703–708.
36. Wettergren A, Schjoldager B, Mortensen P E, Myhre J, Christiansen J, Holst J J. Truncated GLP-1 (proglucagon 72–107amide) inhibits gastric and pancreatic functions in man. Dig Dis Sci 1993; 38:665–673.
37. Layer P, Holst J J, Grandt D, Goebell H: Ileal release of glucagon-like peptide-1 (GLP-1): association with inhibition of gastric acid in humans. Dig Dis Sci 1995; 40: 1074–1082.
38. Layer P, Holst J J. GLP-1: A humoral mediator of the ileal brake in humans? Digestion 1993; 54: 385–386.
39. Nauck M, Ettler R, Niedereichholz U, Ørskov C, Holst J J, Schmiegel W. Inhibition of gastric emptying by GLP-1(7–36 amide) or (7–37): effects on postprandial glycaemia and insulin secretion. Abstract. Gut 1995; 37 (suppl. 2): A124.
40. Schick R R, vorm Walde T, Zimmermann J P, Schusdziarra V, Classen M. Glucagon-like peptide 1—a novel brain peptide involved in feeding regulation. in Ditschuneit H, Gries F A, Hauner H, Schusdziarra V, Wechsler J G (eds.) Obesity in Europe. John Libbey & Company ltd, 1994; pp. 363–367.
41. Tang-Christensen M, Larsen P J, Göke R, Fink-Jensen A, Jessop D S, Møller M, Sheikh S. Brain GLP-1(7–36) amide receptors play a major role in regulation of food and water intake. Am. J. Physiol., 1996, in press.
42. Turton M D, O'Shea D, Gunn I, Beak S A, Edwards C M B, Meeran K, et al. A role for glucagon-like peptide-1 in the regulation of feeding. Nature 1996; 379: 69–72.
43. Willms B, Werner J, Creutzfeldt W, Ørskov C, Holst J J, Nauck M. Inhibition of gastric emptying by glucagon-like peptide-1 (7–36 amide) in patients with type-2-diabetes mellitus. Diabetologia 1994; 37, suppl. 1: A118.

44. Larsen J, Jallad N, Damsbo P. One-week continuous infusion of GLP-1(7–37) improves glycaemic control in NIDDM. Diabetes 1996; 45, suppl. 2: 233A.
45. Ritzel R, Ørskov C, Holst J J, Nauck M A. Pharmacokinetic, insulinotropic, and glucagonostatic properties of GLP-1 [7–36 amide] after subcutaneous injection in healthy volunteers. Dose-response relationships. Diabetologia 1995; 38: 720–725.
46. Deacon C F, Johnsen A H, Holst J J. Degradation of glucagon-like peptide-1 by human plasma in vitro yields an N-terminally truncated peptide that is a major endogenous metabolite in vivo. J Clin Endocrinol Metab 1995; 80: 952–957.
47. Deacon C F, Nauck M A, Toft-Nielsen M, Pridal L, Willms B, Holst J J. 1995. Both subcutaneous and intravenously administered glucagon-like peptide-1 are rapidly degraded from the amino terminus in type II diabetic patients and in healthy subjects. Diabetes 44: 1126–1131.

SUMMARY OF THE INVENTION

Human GLP-1 is a 37 amino acid residue peptide originating from preproglucagon which is synthesised i.a. in the L-cells in the distal ileum, in the pancreas and in the brain. Processing of preproglucagon to give GLP-1(7–36)amide, GLP-1(7–37) and GLP-2 occurs mainly in the L-cells. A simple system is used to describe fragments and analogues of this peptide. Thus, for example, $Gly^8$-GLP-1(7–37) designates a fragment of GLP-1 formally derived from GLP-1 by deleting the amino acid residues Nos. 1 to 6 and substituting the naturally occurring amino acid residue in position 8 (Ala) by Gly. Similarly, $Lys^{34}(N^\epsilon$-tetradecanoyl)-GLP-1 (7–37) designates GLP-1(7–37) wherein the $\epsilon$-amino group of the Lys residue in position 34 has been tetradecanoylated. Where reference in this text is made to C-terminally extended GLP-1 analogues, the amino acid residue in position 38 in Arg unless otherwise indicated, the optional amino acid residue in position 39 is also Arg unless otherwise indicated and the optional amino acid residue in position 40 is Asp unless otherwise indicated. Also, if a C-terminally extended analogue extends to position 41, 42, 43, 44 or 45, the amino acid sequence of this extension is as in the corresponding sequence in human preproglucagon unless otherwise indicated.

In its broadest aspect, the present invention relates to derivatives of GLP-1 and analogues thereof. The derivatives according to the invention have interesting pharmacological properties, in particular they have a more protracted profile of action than the parent peptides.

In the present text, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both.

The term "derivative" is used in the present text to designate a peptide in which one or more of the amino acid residues of the parent peptide have been chemically modified, e.g. by alkylation, acylation, ester formation or amide formation.

The term "a GLP-1 derivative" is used in the present text to designate a derivative of GLP-1 or an analogue thereof. In the present text, the parent peptide from which such a derivative is formally derived is in some places referred to as the "GLP-1 moiety" of the derivative.

In a preferred embodiment, the present invention relates to a GLP-1 derivative wherein at least one amino acid residue of the parent peptide has a lipophilic substituent attached with the proviso that if only one lipophilic substituent is present and this substituent is attached to the N-terminal or to the C-terminal amino acid residue of the parent peptide then this substituent is an alkyl group or a group which has an $\omega$-carboxylic acid group.

In another preferred embodiment, the present invention relates to a GLP-1 derivative having only one lipophilic substituent.

In another preferred embodiment, the present invention relates to a GLP-1 derivative having only one lipophilic substituent which substituent is an alkyl group or a group which has an $\omega$-carboxylic acid group and is attached to the N-terminal amino acid residue of the parent peptide.

In another preferred embodiment, the present invention relates to a GLP-1 derivative having only one lipophilic substituent which substituent is an alkyl group or a group which has an $\omega$-carboxylic acid group and is attached to the C-terminal amino acid residue of the parent peptide.

In another preferred embodiment, the present invention relates to a GLP-1 derivative having only one lipophilic substituent which substituent can be attached to any one amino acid residue which is not the N-terminal or C-terminal amino acid residue of the parent peptide.

In another preferred embodiment, the present invention relates to a GLP-1 derivative wherein two lipophilic substituents are present.

In another preferred embodiment, the present invention relates to a GLP-1 derivative wherein two lipophilic substituents are present, one being attached to the N-terminal amino acid residue while the other is attached to the C-terminal amino acid residue.

In another preferred embodiment, the present invention relates to a GLP-1 derivative wherein two lipophilic substituents are present, one being attached to the N-terminal amino acid residue while the other is attached to an amino acid residue which is not N-terminal or the C-terminal amino acid residue.

In another preferred embodiment, the present invention relates to a GLP-1 derivative wherein two lipophilic substituents are present, one being attached to the C-terminal amino acid residue while the other is attached to an amino acid residue which is not the N-terminal or the C-terminal amino acid residue.

In a further preferred embodiment, the present invention relates to a derivative of GLP-1(7-C), wherein C is selected from the group comprising 38, 39, 40, 41, 42, 43, 44 and 45 which derivative has just one lipophilic substituent which is attached to the C-terminal amino acid residue of the parent peptide.

In a further preferred embodiment, the present invention relates to a GLP-1 derivative, being a derivative of GLP-1 (7-C), wherein C is 35 or 36 which derivative has just one lipophilic substituent which is attached to the C-terminal amino acid residue.

In a further preferred embodiment, the present invention relates to a GLP-1 derivative wherein the lipophilic substituent comprises from 4 to 40 carbon atoms, more preferred from 8 to 25 carbon atoms.

In a further preferred embodiment, the present invention relates to a GLP-1 derivative wherein a lipophilic substituent is attached to an amino acid residue in such a way that a carboxyl group of the lipophilic substituent forms an amide bond with an amino group of the amino acid residue.

In a further preferred embodiment, the present invention relates to a GLP-1 derivative wherein a lipophilic substituent is attached to an amino acid residue in such a way that an amino group of the lipophilic substituent forms an amide bond with a carboxyl group of the amino acid residue.

In a further preferred embodiment, the present invention relates to a GLP-1 derivative wherein a lipophilic substituent is attached to the parent peptide by means of a spacer.

In a further preferred embodiment, the present invention relates to a GLP-1 derivative wherein a lipophilic substituent—optionally via a spacer—is attached to the ε-amino group of a Lys residue contained in the parent peptide.

In a further preferred embodiment, the present invention relates to a GLP-1 derivative wherein a lipophilic substituent is attached to the parent peptide by means of a spacer which is an unbranched alkane $\alpha,\omega$-dicarboxylic acid group having from 1 to 7 methylene groups, preferably two methylene groups which spacer forms a bridge between an amino group of the parent peptide and an amino group of the lipophilic substituent.

In a further preferred embodiment, the present invention relates to a GLP-1 derivative wherein a lipophilic substituent is attached to the parent peptide by means of a spacer which is an amino acid residue except Cys, or a dipeptide such as Gly-Lys. In the present text, the expression "a dipeptide such as Gly-Lys" is used to designate a dipeptide wherein the C-terminal amino acid residue is Lys, His or Trp, preferably Lys, and wherein the N-terminal amino acid residue is selected from the group comprising Ala, Arg, Asp, Asn, Gly, Glu, Gln, Ile, Leu, Val, Phe and Pro.

In a further preferred embodiment, the present invention relates to a GLP-1 derivative wherein a lipophilic substituent is attached to the parent peptide by means of a spacer which is an amino acid residue except Cys, or is a dipeptide such as Gly-Lys and wherein a carboxyl group of the parent peptide forms an amide bond with an amino group of a Lys residue or a dipeptide containing a Lys residue, and the other amino group of the Lys residue or a dipeptide containing a Lys residue forms an amide bond with a carboxyl group of the lipophilic substituent.

In a further preferred embodiment, the present invention relates to a GLP-1 derivative wherein a lipophilic substituent is attached to the parent peptide by means of a spacer which is an amino acid residue except Cys, or is a dipeptide such as Gly-Lys and wherein an amino group of the parent peptide forms an amide bond with a carboxylic group of the amino acid residue or dipeptide spacer, and an amino group of the amino acid residue or dipeptide spacer forms an amide bond with a carboxyl group of the lipophilic substituent.

In a further preferred embodiment, the present invention relates to a GLP-1 derivative wherein a lipophilic substituent is attached to the parent peptide by means of a spacer which is an amino acid residue except Cys, or is a dipeptide such as Gly-Lys and wherein a carboxyl group of the parent peptide forms an amide bond with an amino group of the amino acid residue spacer or dipeptide spacer, and the carboxyl group of the amino acid residue spacer or dipeptide spacer forms an amide bond with an amino group of the lipophilic substituent.

In a further preferred embodiment, the present invention relates to a GLP-1 derivative wherein a lipophilic substituent is attached to the parent peptide by means of a spacer which is an amino acid residue except Cys, or is a dipeptide such as Gly-Lys, and wherein a carboxyl group of the parent peptide forms an amide bond with an amino group of a spacer which is Asp or Glu, or a dipeptide spacer containing an Asp or Glu residue, and a carboxyl group of the spacer forms an amide bond with an amino group of the lipophilic substituent.

In a further preferred embodiment, the present invention relates to a GLP-1 derivative having a lipophilic substituent which comprises a partially or completely hydrogenated cyclopentanophenathrene skeleton.

In a further preferred embodiment, the present invention relates to a GLP-1 derivative having a lipophilic substituent which is a straight-chain or branched alkyl group.

In a further preferred embodiment, the present invention relates to a GLP-1 derivative having a lipophilic substituent which is the acyl group of a straight-chain or branched fatty acid.

In a further preferred embodiment, the present invention relates to a GLP-1 derivative having a lipophilic substituent which is an acyl group selected from the group comprising $CH_3(CH_2)_nCO-$, wherein n is an integer from 4 to 38, preferably an integer from 4 to 24, more preferred selected from the group comprising $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.

In a further preferred embodiment, the present invention relates to a GLP-1 derivative having a lipophilic substituent which is an acyl group of a straight-chain or branched alkane $\alpha,\omega$-dicarboxylic acid.

In a further preferred embodiment, the present invention relates to a GLP-1 derivative having a lipophilic substituent which is an acyl group selected from the group comprising $HOOC(CH_2)_mCO-$, wherein m is an integer from 4 to 38, preferably an integer from 4 to 24, more preferred selected from the group comprising $HOOC(CH_2)_{14}CO-$, $HOOC(CH_2)_{16}CO-$, $HOOC(CH_2)_{18}CO-$, $HOOC(CH_2)_{20}CO-$ and $HOOC(CH_2)_{22}CO-$.

In a further preferred embodiment, the present invention relates to a GLP-1 derivative having a lipophilic substituent which is a group of the formula $CH_3(CH_2)_p((CH_2)_qCOOH)CHNH-CO(CH_2)_2CO-$, wherein p and q are integers and p+q is an integer of from 8 to 33, preferably from 12 to 28.

In a further preferred embodiment, the present invention relates to a GLP-1 derivative having a lipophilic substituent which is a group of the formula $CH_3(CH_2)_rCO-NHCH(COOH)(CH_2)_2CO-$, wherein r is an integer of from 10 to 24.

In a further preferred embodiment, the present invention relates to a GLP-1 derivative having a lipophilic substituent which is a group of the formula $CH_3(CH_2)_sCO-NHCH((CH_2)_2COOH)CO-$, wherein s is an integer of from 8 to 24.

In a further preferred embodiment, the present invention relates to a GLP-1 derivative having a lipophilic substituent which is a group of the formula $COOH(CH_2)_tCO-$ wherein t is an integer of from 8 to 24.

In a further preferred embodiment, the present invention relates to a GLP-1 derivative having a lipophilic substituent which is a group of the formula $-NHCH(COOH)(CH_2)_4NH-CO(CH_2)_uCH_3$, wherein u is an integer of from 8 to 18.

In a further preferred embodiment, the present invention relates to a GLP-1 derivative having a lipophilic substituent which is a group of the formula $-NHCH(COOH)(CH_2)_4NH-COCH((CH_2)_2COOH)NH-CO(CH_2)_wCH_3$, wherein w is an integer of from 10 to 16.

In a further preferred embodiment, the present invention relates to a GLP-1 derivative having a lipophilic substituent which is a group of the formula —NHCH(COOH)(CH$_2$)$_4$NH—CO(CH$_2$)$_2$CH(COOH)NH—CO(CH$_2$)$_x$CH$_3$, wherein x is an integer of from 10 to 16.

In a further preferred embodiment, the present invention relates to a GLP-1 derivative having a lipophilic substituent which is a group of the formula —NHCH(COOH)(CH$_2$)$_4$NH—CO(CH$_2$)$_2$CH(COOH)NHCO(CH$_2$)$_y$CH$_3$, wherein y is zero or an integer of from 1 to 22.

In a further preferred embodiment, the present invention relates to a GLP-1 derivative having a lipophilic substituent which can be negatively charged. Such a lipophilic substituent can for example be a substituent which has a carboxyl group.

In a further preferred embodiment, the present invention relates to a GLP-1 derivative the parent peptide of which is selected from the group comprising GLP-1(1–45) or an analogue thereof.

In a further preferred embodiment, the present invention relates to a GLP-1 derivative derived from a GLP-1 fragment selected from the group comprising GLP-1(7–35), GLP-1(7–36), GLP-1(7–36)amide, GLP-1(7–37), GLP-1(7–38), GLP-1(7–39), GLP-1(7–40) and GLP-1(7–41) or an analogue thereof.

In a further preferred embodiment, the present invention relates to a GLP-1 analogue derived from a GLP-1 analogue selected from the group comprising GLP-1(1–35), GLP-1(1–36), GLP-1(1–36)amide, GLP-1(1–37), GLP-1(1–38), GLP-1(1–39), GLP-1(1–40) and GLP-1(1–41) or an analogue thereof.

In a further preferred embodiment, the present invention relates to a GLP-1 derivative wherein the designation analogue comprises derivatives wherein a total of up to fifteen, preferably up to ten amino acid residues have been exchanged with any α-amino acid residue.

In a further preferred embodiment, the present invention relates to a GLP-1 derivative wherein the designation analogue comprises derivatives wherein a total of up to fifteen, preferably up to ten amino acid residues have been exchanged with any α-amino acid residue which can be coded for by the genetic code.

In a further preferred embodiment, the present invention relates to a GLP-1 derivative wherein the designation analogue comprises derivatives wherein a total of up to six amino acid residues have been exchanged with another α-amino acid residue which can be coded for by the genetic code.

In a further preferred embodiment, the present invention relates to a GLP-1(A–B) derivative wherein A is an integer from 1 to 7 and B is an integer from 38 to 45 or an analogue thereof comprising one lipophilic substituent attached to the C-terminal amino acid residue and, optionally, a second lipophilic substituent attached to one of the other amino acid residues.

In a further preferred embodiment, a parent peptide for a derivative according to the invention is selected from the group comprising Arg$^{26}$-GLP-1(7–37); Arg$^{34}$-GLP-1(7–37); Lys$^{36}$-GLP-1(7–37); Arg$^{26,34}$Lys$^{36}$-GLP-1(7–37); Arg$^{26,34}$Lys$^{38}$GLP-1(7–38); Arg$^{26,34}$Lys$^{39}$-GLP-1(7–39); Arg$^{26,34}$Lys$^{40}$-GLP-1(7–40); Arg$^{26}$Lys$^{36}$-GLP-1(7–37); Arg$^{34}$Lys$^{36}$-GLP-1(7–37); Arg$^{26}$Lys$^{39}$-GLP-1(7–39); Arg$^{34}$Lys$^{40}$-GLP-1(7–40); Arg$^{26,34}$Lys$^{36,39}$-GLP-1(7–39); Arg$^{26,34}$Lys$^{36,40}$-GLP-1(7–40); Gly$^8$Arg26-GLP-1(7–37); Gly$^8$Arg$^{34}$-GLP-1(7–37); Gly$^8$Lys$^{36}$-GLP-1(7–37); Gly$^8$Arg$^{26,34}$Lys$^{36}$-GLP-1(7–37); Gly$^8$Arg$^{26,34}$Lys$^{39}$-GLP-1(7–39); Gly$^8$Arg$^{26,34}$Lys$^{40}$-GLP-1(7–40); Gly$^8$Arg$^{26}$Lys$^{36}$-GLP-1(7–37); Gly$^8$Arg$^{34}$Lys$^{36}$-GLP-1(7–37); Gly$^8$Arg$^{26}$Lys$^{39}$-GLP-1(7–39); Gly$^8$Arg$^{34}$Lys$^{40}$-GLP-1(7–40); Gly$^8$Arg$^{26,34}$Lys$^{36,39}$-GLP-1(7–39) and Gly$^8$Arg$^{26,34}$Lys$^{36,40}$-GLP-1(7–40).

In a further preferred embodiment, a parent peptide for a derivative according to the invention is selected from the group comprising Arg$^{26,34}$Lys$^{38}$GLP-1(7–38); Arg$^{26,34}$Lys$^{39}$GLP-1(7–39); Arg$^{26,34}$Lys$^{40}$GLP-1(7–40); Arg$^{26,34}$Lys$^{41}$GLP-1(7–41); Arg$^{26,34}$Lys$^{42}$GLP-1(7–42); Arg$^{26,34}$Lys$^{43}$GLP-1(7–43); Arg$^{26,34}$Lys$^{44}$GLP-1(7–44); Arg$^{26,34}$Lys$^{45}$GLP-1(7–45); Arg$^{26,34}$Lys$^{38}$GLP-1(1–38); Arg$^{26,34}$Lys$^{39}$GLP-1(1–39); Arg$^{26,34}$Lys$^{40}$GLP-1(1–40); Arg$^{26,34}$Lys$^{41}$GLP-1(1–41); Arg$^{26,34}$Lys$^{42}$GLP-1(1–42); Arg$^{26,34}$Lys$^{43}$GLP-1(1–43); Arg$^{26,34}$Lys$^{44}$GLP-1(1–44); Arg$^{26,34}$Lys$^{45}$GLP-1(1–45); Arg$^{26,34}$Lys$^{38}$GLP-1(2–38); Arg$^{26,34}$Lys$^{39}$GLP-1(2–39); Arg$^{26,34}$Lys$^{40}$GLP-1(2–40); Arg$^{26,34}$Lys$^{41}$GLP-1(2–41); Arg$^{26,34}$Lys$^{42}$GLP-1(2–42); Arg$^{26,34}$Lys$^{43}$GLP-1(2–43); Arg$^{26,34}$Lys$^{44}$GLP-1(2–44); Arg$^{26,34}$Lys$^{45}$GLP-1(2–45); Arg$^{26,34}$Lys$^{38}$GLP-1(3–38); Arg$^{26,34}$Lys$^{39}$GLP-1(3–39); Arg$^{26,34}$Lys$^{40}$GLP-1(3–40); Arg$^{26,34}$Lys$^{41}$GLP-1(3–41); Arg$^{26,34}$Lys$^{42}$GLP-1(3–42); Arg$^{26,34}$Lys$^{43}$GLP-1(3–43); Arg$^{26,34}$Lys$^{44}$GLP-1(3–44); Arg$^{26,34}$Lys$^{45}$GLP-1(3–45); Arg$^{26,34}$Lys$^{38}$GLP-1(4–38); Arg$^{26,34}$Lys$^{39}$GLP-1(4–39); Arg$^{26,34}$Lys$^{40}$GLP-1(4–40); Arg$^{26,34}$Lys$^{41}$GLP-1(4–41); Arg$^{26,34}$Lys$^{42}$GLP-1(4–42); Arg$^{26,34}$Lys$^{43}$GLP-1(4–43); Arg$^{26,34}$Lys$^{44}$GLP-1(4–44); Arg$^{26,34}$Lys$^{45}$GLP-1(4–45); Arg$^{26,34}$Lys$^{38}$GLP-1(5–38); Arg$^{26,34}$Lys$^{39}$GLP-1(5–39); Arg$^{26,34}$Lys$^{40}$GLP-1(5–40); Arg$^{26,34}$Lys$^{41}$GLP-1(5–41); Arg$^{26,34}$Lys$^{42}$GLP-1(5–42); Arg$^{26,34}$Lys$^{43}$GLP-1(5–43); Arg$^{26,34}$Lys$^{44}$GLP-1(5–44); Arg$^{26,34}$Lys$^{45}$GLP-1(5–45); Arg$^{26,34}$Lys$^{38}$GLP-1(6–38); Arg$^{26,34}$Lys$^{39}$GLP-1(6–39); Arg$^{26,34}$Lys$^{40}$GLP-1(6–40); Arg$^{26,34}$Lys$^{41}$GLP-1(6–41); Arg$^{26,34}$Lys$^{42}$GLP-1(6–42); Arg$^{26,34}$Lys$^{43}$GLP-1(6–43); Arg$^{26,34}$Lys$^{44}$GLP-1(6–44); Arg$^{26,34}$Lys$^{45}$GLP-1(6–45); Arg$^{26}$Lys$^{38}$GLP-1(1–38); Arg$^{34}$Lys$^{38}$GLP-1(1–38); Arg$^{26,34}$Lys$^{36,38}$GLP-1(1–38); Arg$^{26}$Lys$^{38}$GLP-1(7–38); Arg$^{34}$Lys$^{38}$GLP-1(7–38); Arg$^{26,34}$Lys$^{36,38}$GLP-1(7–38); Arg$^{26,34}$Lys$^{38}$GLP-1(7–38); Arg$^{26}$Lys$^{39}$GLP-1(1–39); Arg$^{34}$Lys$^{39}$GLP-1(1–39); Arg$^{26,34}$Lys$^{36,39}$GLP-1(1–39); Arg$^{26}$Lys$^{39}$GLP-1(7–39); Arg$^{34}$Lys$^{39}$GLP-1(7–39) and Arg$^{26,34}$Lys$^{36,39}$GLP-1(7–39).

In a further preferred embodiment, the present invention relates to a GLP-1 derivative wherein the parent peptide is selected from the group comprising Arg$^{26}$-GLP-1(7–37), Arg$^{34}$-GLP-1(7–37), Lys$^{36}$-GLP-1(7–37), Arg$^{26,34}$Lys$^{36}$-GLP-1(7–37), Arg$^{26}$Lys$^{36}$-GLP-1(7–37), Arg$^{34}$Lys$^{36}$-GLP-1(7–37), Gly$^8$Arg$^{26}$-GLP-1(7–37), Gly$^8$Arg$^{34}$-GLP-1(7–37), Gly$^8$Lys$^{36}$-GLP-1(7–37), Gly$^8$Arg$^{26,34}$Lys$^{36}$-GLP-1(7–37), Gly$^8$Arg$^{26}$Lys$^{36}$-GLP-1(7–37) and Gly$^8$Arg$^{34}$Lys$^{36}$-GLP-1(7–37).

In a further preferred embodiment, the present invention relates to a GLP-1 derivative wherein the parent peptide is selected from the group comprising Arg$^{26}$Lys$^{38}$-GLP-1(7–38), Arg$^{26,34}$Lys$^{38}$-GLP-1(7–38), Arg$^{26,34}$Lys$^{36,38}$-GLP-1(7–38), Gly$^8$Arg$^{26}$Lys$^{38}$-GLP-1(7–38) and Gly$^8$Arg$^{26,34}$Lys$^{36,38}$-GLP-1(7–38).

In a further preferred embodiment, the present invention relates to a GLP-1 derivative wherein the parent peptide is selected from the group comprising Arg$^{26}$Lys$^{39}$-GLP-1(7–39), Arg$^{26,34}$Lys$^{36,39}$-GLP-1(7–39), Gly$^8$Arg$^{26}$Lys$^{39}$-GLP-1(7–39) and Gly$^8$Arg$^{26,34}$Lys$^{36,39}$-GLP-1(7–39).

In a further preferred embodiment, the present invention relates to a GLP-1 derivative wherein the parent peptide is selected from the group comprising Arg$^{34}$Lys$^{40}$-GLP-1(7–40), Arg$^{26,34}$Lys$^{36,40}$-GLP-1(7–40), Gly$^8$Arg$^{34}$Lys$^{40}$-GLP-1(7–40) and Gly$^8$Arg$^{26,34}$Lys$^{36,40}$-GLP-1(7–40).

In a further preferred embodiment, the present invention relates to a GLP-1 derivative which is selected from the group comprising:

Lys²⁶(Nᵋ-tetradecanoyl)-GLP-1(7–37);
Lys³⁴(Nᵋ-tetradecanoyl)-GLP-1(7–37);
Lys²⁶,³⁴-bis(Nᵋ-tetradecanoyl)-GLP-1(7–37);
Gly⁸Lys²⁶(Nᵋ-tetradecanoyl)-GLP-1(7–37);
Gly⁸Lys³⁴(Nᵋ-tetradecanoyl)-GLP-1(7–37);
Gly⁸Lys²⁶,³⁴-bis(Nᵋ-tetradecanoyl)-GLP-1(7–37);
Arg²⁶Lys³⁴(Nᵋ-tetradecanoyl)-GLP-1(7–37);
Lys²⁶(Nᵋ-tetradecanoyl)-GLP-1(7–38);
Lys³⁴(Nᵋ-tetradecanoyl)-GLP-1(7–38);
Lys²⁶,³⁴-bis(Nᵋ-tetradecanoyl)-GLP-1(7–38);
Gly⁸Lys²⁶(Nᵋ-tetradecanoyl)-GLP-1(7–38);
Gly⁸Lys³⁴(Nᵋ-tetradecanoyl)-GLP-1(7–38);
Gly⁸Lys²⁶,³⁴-bis(Nᵋ-tetradecanoyl)-GLP-1(7–38);
Arg²⁶Lys³⁴(Nᵋ-tetradecanoyl)-GLP-1(7–38);
Lys²⁶(Nᵋ-tetradecanoyl)-GLP-1(7–39);
Lys³⁴(Nᵋ-tetradecanoyl)-GLP-1(7–39);
Lys²⁶,³⁴-bis(Nᵋ-tetradecanoyl)-GLP-1(7–39);
Gly⁸Lys²⁶(Nᵋ-tetradecanoyl)-GLP-1(7–39);
Gly⁸Lys³⁴(Nᵋ-tetradecanoyl)-GLP-1(7–39);
Gly⁸Lys²⁶,³⁴-bis(Nᵋ-tetradecanoyl)-GLP-1(7–39);
Arg²⁶Lys³⁴(Nᵋ-tetradecanoyl)-GLP-1(7–39);
Lys²⁶(Nᵋ-tetradecanoyl)-GLP-1(7–40);
Lys³⁴(Nᵋ-tetradecanoyl)-GLP-1(7–40);
Lys²⁶,³⁴-bis(Nᵋ-tetradecanoyl)-GLP-1(7–40);
Gly⁸Lys²⁶(Nᵋ-tetradecanoyl)-GLP-1(7–40);
Gly⁸Lys³⁴(Nᵋ-tetradecanoyl)-GLP-1(7–40);
Gly⁸Lys²⁶,³⁴-bis(Nᵋ-tetradecanoyl)-GLP-1(7–40);
Arg²⁶Lys³⁴(Nᵋ-tetradecanoyl)-GLP-1(7–40);
Lys²⁶(Nᵋ-tetradecanoyl)-GLP-1(7–36);
Lys³⁴(Nᵋ-tetradecanoyl)-GLP-1(7–36);
Lys²⁶,³⁴-bis(Nᵋ-tetradecanoyl)-GLP-1(7–36);
Gly⁸Lys²⁶(Nᵋ-tetradecanoyl)-GLP-1(7–36);
Gly⁸Lys³⁴(Nᵋ-tetradecanoyl)-GLP-1(7–36);
Gly⁸Lys²⁶,³⁴-bis(Nᵋ-tetradecanoyl)-GLP-1(7–36);
Arg²⁶Lys³⁴(Nᵋ-tetradecanoyl)-GLP-1(7–36);
Lys²⁶(Nᵋ-tetradecanoyl)-GLP-1(7–35);
Lys³⁴(Nᵋ-tetradecanoyl)-GLP-1(7–35);
Lys²⁶,³⁴-bis(Nᵋ-tetradecanoyl)-GLP-1(7–35);
Gly⁸Lys²⁶(Nᵋ-tetradecanoyl)-GLP-1(7–35);
Gly⁸Lys³⁴(Nᵋ-tetradecanoyl)-GLP-1(7–35);
Gly⁸Lys²⁶,³⁴-bis(Nᵋ-tetradecanoyl)-GLP-1(7–35);
Arg²⁶Lys³⁴(Nᵋ-tetradecanoyl)-GLP-1(7–35);
Lys²⁶(Nᵋ-tetradecanoyl)-GLP-1(7–36)amide;
Lys³⁴(Nᵋ-tetradecanoyl)-GLP-1(7–36)amide;
Lys²⁶,³⁴-bis(Nᵋ-tetradecanoyl)-GLP-1(7–36)amide;
Gly⁸Lys²⁶(Nᵋ-tetradecanoyl)-GLP-1(7–36)amide;
Gly⁸Lys³⁴(Nᵋ-tetradecanoyl)-GLP-1(7–36)amide;
Gly⁸Lys²⁶,³⁴-bis(Nᵋ-tetradecanoyl)-GLP-1(7–36)amide;
Arg²⁶Lys³⁴(Nᵋ-tetradecanoyl)-GLP-1(7–36)amide;
Gly⁸Arg²⁶Lys³⁴(Nᵋ-tetradecanoyl)-GLP-1(7–37);
Lys²⁶(Nᵋ-tetradecanoyl)Arg³⁴-GLP-1(7–37);
Gly⁸Lys²⁶(Nᵋ-tetradecanoyl)Arg³⁴-GLP-1(7–37);
Arg²⁶,³⁴Lys³⁶(Nᵋ-tetradecanoyl)-GLP-1(7–37);
Gly⁸Arg²⁶,³⁴Lys³⁶(Nᵋ-tetradecanoyl)-GLP-1(7–37);
Gly⁸Arg²⁶,³⁴Lys³⁴(Nᵋ-tetradecanoyl)-GLP-1(7–38);
Lys²⁶(Nᵋ-tetradecanoyl)Arg³⁴-GLP-1(7–38);
Gly⁸Lys²⁶(Nᵋ-tetradecanoyl)Arg³⁴-GLP-1(7–38);
Arg²⁶,³⁴Lys³⁶(Nᵋ-tetradecanoyl)-GLP-1(7–38);
Arg²⁶,³⁴Lys³⁸(Nᵋ-tetradecanoyl)-GLP-1(7–38);
Gly⁸Arg²⁶,³⁴Lys³⁶(Nᵋ-tetradecanoyl)-GLP-1(7–38);
Gly⁸Arg²⁶,³⁴Lys³⁴(Nᵋ-tetradecanoyl)-GLP-1(7–39);
Lys²⁶(Nᵋ-tetradecanoyl)Arg³⁴-GLP-1(7–39);
Gly⁸Lys²⁶(Nᵋ-tetradecanoyl)Arg³⁴-GLP-1(7–39);
Arg²⁶,³⁴Lys³⁶(Nᵋ-tetradecanoyl)-GLP-1(7–39);
Gly⁸Arg²⁶,³⁴Lys³⁶(Nᵋ-tetradecanoyl)-GLP-1(7–39);
Gly⁸Arg²⁶,³⁴Lys³⁴(Nᵋ-tetradecanoyl)-GLP-1(7–40);
Lys²⁶(Nᵋ-tetradecanoyl)Arg³⁴-GLP-1(7–40);
Gly⁸Lys²⁶(Nᵋ-tetradecanoyl)Arg³⁴-GLP-1(7–40);
Arg²⁶,³⁴Lys³⁶(Nᵋ-tetradecanoyl)-GLP-1(7–40);
Gly⁸Arg²⁶,³⁴Lys³⁶(Nᵋ-tetradecanoyl)-GLP-1(7–40);
Lys²⁶(Nᵋ-(ω-carboxynonadecanoyl))-GLP-1(7–37);
Lys³⁴(Nᵋ-(ω-carboxynonadecanoyl))-GLP-1(7–37);
Lys²⁶,³⁴-bis(Nᵋ-(ω-carboxynonadecanoyl))-GLP-1(7–37);
Gly⁸Lys²⁶(Nᵋ-(ω-carboxynonadecanoyl))-GLP-1(7–37);
Gly⁸Lys³⁴(Nᵋ-(ω-carboxynonadecanoyl))-GLP-1(7–37);
Gly⁸Lys²⁶,³⁴-bis(Nᵋ-(ω-carboxynonadecanoyl))-GLP-1(7–37);
Lys²⁶(Nᵋ-(ω-carboxynonadecanoyl))-GLP-1(7–38);
Lys³⁴(Nᵋ-(ω-carboxynonadecanoyl))-GLP-1(7–38);
Lys²⁶,³⁴-bis(Nᵋ-(ω-carboxynonadecanoyl))-GLP-1(7–38);
Gly⁸Lys²⁶(Nᵋ-(ω-carboxynonadecanoyl))-GLP-1(7–38);
Gly⁸Lys³⁴(Nᵋ-(ω-carboxynonadecanoyl))-GLP-1(7–38);
Gly⁸Lys²⁶,³⁴-bis(Nᵋ-(ω-carboxynonadecanoyl))-GLP-1(7–38);
Lys²⁶(Nᵋ-(ω-carboxynonadecanoyl))-GLP-1(7–39);
Lys³⁴(Nᵋ-(ω-carboxynonadecanoyl))-GLP-1(7–39);
Lys²⁶,³⁴-bis(Nᵋ-(ω-carboxynonadecanoyl))-GLP-1(7–39);
Gly⁸Lys²⁶(Nᵋ-(ω-carboxynonadecanoyl))-GLP-1(7–39);
Gly⁸Lys³⁴(Nᵋ-(ω-carboxynonadecanoyl))-GLP-1(7–39);
Gly⁸Lys²⁶,³⁴-bis(Nᵋ-(ω-carboxynonadecanoyl))-GLP-1(7–39);
Lys²⁶(Nᵋ-(ω-carboxynonadecanoyl))-GLP-1(7–40);
Lys³⁴(Nᵋ-(ω-carboxynonadecanoyl))-GLP-1(7–40);
Lys²⁶,³⁴-bis(Nᵋ-(ω-carboxynonadecanoyl))-GLP-1(7–40);
Gly⁸Lys²⁶(Nᵋ-(ω-carboxynonadecanoyl))-GLP-1(7–40);
Gly⁸Lys³⁴(Nᵋ-(ω-carboxynonadecanoyl))-GLP-1(7–40);
Gly⁸Lys²⁶,³⁴-bis(Nᵋ-(ω-carboxynonadecanoyl))-GLP-1(7–40);
Lys²⁶(Nᵋ-(ω-carboxynonadecanoyl))-GLP-1(7–36);
Lys³⁴(Nᵋ-(ω-carboxynonadecanoyl))-GLP-1(7–36);
Lys²⁶,³⁴-bis(Nᵋ-(ω-carboxynonadecanoyl))-GLP-1(7–36);
Gly⁸Lys²⁶(Nᵋ-(ω-carboxynonadecanoyl))-GLP-1(7–36);
Gly⁸Lys³⁴(Nᵋ-(ω-carboxynonadecanoyl))-GLP-1(7–36);
Gly⁸Lys²⁶,³⁴-bis(Nᵋ-(ω-carboxynonadecanoyl))-GLP-1(7–36);
Lys²⁶(Nᵋ-(ω-carboxynonadecanoyl))-GLP-1(7–36)amide;
Lys³⁴(Nᵋ-(ω-carboxynonadecanoyl))-GLP-1(7–36)amide;
Lys²⁶,³⁴-bis(Nᵋ-(ω-carboxynonadecanoyl))-GLP-1(7–36)amide;
Gly⁸Lys²⁶(Nᵋ-(ω-carboxynonadecanoyl))-GLP-1(7–36)amide;
Gly⁸Lys³⁴(Nᵋ-(ω-carboxynonadecanoyl))-GLP-1(7–36)amide;
Gly⁸Lys²⁶,³⁴-bis(Nᵋ-(ω-carboxynonadecanoyl))-GLP-1(7–36)amide;
Lys²⁶(Nᵋ-(ω-carboxynonadecanoyl))-GLP-1(7–35);
Lys³⁴(Nᵋ-(ω-carboxynonadecanoyl))-GLP-1(7–35);
Lys²⁶,³⁴-bis(Nᵋ-(ω-carboxynonadecanoyl))-GLP-1(7–35);
Gly⁸Lys²⁶(Nᵋ-(ω-carboxynonadecanoyl))-GLP-1(7–35);
Gly⁸Lys³⁴(Nᵋ-(ω-carboxynonadecanoyl))-GLP-1(7–35);
Gly⁸Lys²⁶,³⁴-bis(Nᵋ-(ω-carboxynonadecanoyl))-GLP-1(7–35);
Arg²⁶Lys³⁴(Nᵋ-(ω-carboxynonadecanoyl))-GLP-1(7–37);
Gly⁸Arg²⁶Lys³⁴(Nᵋ-(ω-carboxynonadecanoyl))-GLP-1(7–37);
Lys²⁶(Nᵋ-(ω-carboxynonadecanoyl))Arg³⁴-GLP-1(7–37);
Gly⁸Lys²⁶(Nᵋ-(ω-carboxynonadecanoyl))Arg³⁴-GLP-1(7–37);
Arg²⁶,³⁴Lys³⁶(Nᵋ-(ω-carboxynonadecanoyl))-GLP-1(7–37);
Gly⁸Arg²⁶,³⁴Lys³⁶(Nᵋ-(ω-carboxynonadecanoyl))-GLP-1(7–37);
Arg²⁶Lys³⁴(Nᵋ-(ω-carboxynonadecanoyl))-GLP-1(7–38);

Gly$^8$Arg$^{26}$Lys$^{34}$(N$^\epsilon$-(ω-carboxynonadecanoyl))-GLP-1(7–38);
Lys$^{26}$(N$^\epsilon$-(ω-carboxynonadecanoyl))Arg$^{34}$-GLP-1(7–38);
Gly$^8$Lys$^{26}$(N$^\epsilon$-(ω-carboxynonadecanoyl))Arg$^{34}$-GLP-1(7–38);
Arg$^{26,34}$Lys$^{36}$(N$^\epsilon$-(ω-carboxynonadecanoyl))-GLP-1(7–38);
Arg$^{26,34}$Lys$^{38}$(N$^\epsilon$-(ω-carboxynonadecanoyl))-GLP-1(7–38);
Gly$^8$Arg$^{26,34}$Lys$^{36}$(N$^\epsilon$-(ω-carboxynonadecanoyl))-GLP-1(7–38);
Arg$^{26}$Lys$^{34}$(N$^\epsilon$-(ω-carboxynonadecanoyl))-GLP-1(7–39);
Gly$^8$Arg$^{26}$Lys$^{34}$(N$^\epsilon$-(ω-carboxynonadecanoyl))-GLP-1(7–39);
Lys$^{26}$(N$^\epsilon$-(ω-carboxynonadecanoyl))Arg$^{34}$-GLP-1(7–39);
Gly$^8$Lys$^{26}$(N$^\epsilon$-(ω-carboxynonadecanoyl))Arg$^{34}$-GLP-1(7–39);
Arg$^{26,34}$Lys$^{36}$(N$^\epsilon$-(ω-carboxynonadecanoyl))-GLP-1(7–39);
Gly$^8$Arg$^{26,34}$Lys$^{36}$(N$^\epsilon$-(ω-carboxynonadecanoyl))-GLP-1(7–39);
Arg$^{26}$Lys$^{34}$(N$^\epsilon$-(ω-carboxynonadecanoyl))-GLP-1(7–40);
Gly$^8$Arg$^{26}$Lys$^{34}$(N$^\epsilon$-(ω-carboxynonadecanoyl))-GLP-1(7–40);
Lys$^{26}$(N$^\epsilon$-(ω-carboxynonadecanoyl))Arg$^{34}$-GLP-1(7–40);
Gly$^8$Lys$^{26}$(N$^\epsilon$-(ω-carboxynonadecanoyl))Arg$^{34}$-GLP-1(7–40);
Arg$^{26,34}$Lys$^{36}$(N$^\epsilon$-(ω-carboxynonadecanoyl))-GLP-1(7–40);
Gly$^8$Arg$^{26,34}$Lys$^{36}$(N$^\epsilon$-(ω-carboxynonadecanoyl))-GLP-1(7–40);
Lys$^{26}$(N$^\epsilon$-(7-deoxycholoyl))-GLP-1(7–37);
Lys$^{34}$(N$^\epsilon$-(7-deoxycholoyl))-GLP-1(7–37);
Lys$^{26,34}$-bis(N$^\epsilon$-(7-deoxycholoyl))-GLP-1(7–37);
Gly$^8$Lys$^{26}$(N$^\epsilon$-(7-deoxycholoyl))-GLP-1(7–37);
Gly$^8$Lys$^{34}$(N$^\epsilon$-(7-deoxycholoyl))-GLP-1(7–37);
Gly$^8$Lys$^{26,34}$-bis(N$^\epsilon$-(7-deoxycholoyl))-GLP-1(7–37);
Arg$^{26}$Lys$^{34}$(N$^\epsilon$-(7-deoxycholoyl))-GLP-1(7–37);
Lys$^{26}$(N$^\epsilon$-(7-deoxycholoyl))-GLP-1(7–38);
Lys$^{34}$(N$^\epsilon$-(7-deoxycholoyl))-GLP-1(7–38);
Lys$^{26,34}$-bis(N$^\epsilon$-(7-deoxycholoyl))-GLP-1(7–38);
Gly$^8$Lys$^{26}$(N$^\epsilon$-(7-deoxycholoyl))-GLP-1(7–38);
Gly$^8$Lys$^{34}$(N$^\epsilon$-(7-deoxycholoyl))-GLP-1(7–38);
Gly$^8$Lys$^{26,34}$-bis(N$^\epsilon$-(7-deoxycholoyl))-GLP-1(7–38);
Arg$^{26}$Lys$^{34}$(N$^\epsilon$-(7-deoxycholoyl))-GLP-1(7–38);
Lys$^{26}$(N$^\epsilon$-(7-deoxycholoyl))-GLP-1(7–39);
Lys$^{34}$(N$^\epsilon$-(7-deoxycholoyl))-GLP-1(7–39);
Lys$^{26,34}$-bis(N$^\epsilon$-(7-deoxycholoyl))-GLP-1(7–39);
Gly$^8$Lys$^{26}$(N$^\epsilon$-(7-deoxycholoyl))-GLP-1(7–39);
Gly$^8$Lys$^{34}$(N$^\epsilon$-(7-deoxycholoyl))-GLP-1(7–39);
Gly$^8$Lys$^{26,34}$-bis(N$^\epsilon$-(7-deoxycholoyl))-GLP-1(7–39);
Arg$^{26}$Lys$^{34}$(N$^\epsilon$-(7-deoxycholoyl))-GLP-1(7–39);
Lys$^{26}$(N$^\epsilon$-(7-deoxycholoyl))-GLP-1(7–40);
Lys$^{34}$(N$^\epsilon$-(7-deoxycholoyl))-GLP-1(7–40);
Lys$^{26,34}$-bis(N$^\epsilon$-(7-deoxycholoyl))-GLP-1(7–40);
Gly$^8$Lys$^{26}$(N$^\epsilon$-(7-deoxycholoyl))-GLP-1(7–40);
Gly$^8$Lys$^{34}$(N$^\epsilon$-(7-deoxycholoyl))-GLP-1(7–40);
Gly$^8$Lys$^{26,34}$-bis(N$^\epsilon$-(7-deoxycholoyl))-GLP-1(7–40);
Arg$^{26}$Lys$^{34}$(N$^\epsilon$-(7-deoxycholoyl))-GLP-1(7–40);
Lys$^{26}$(N$^\epsilon$-(7-deoxycholoyl))-GLP-1(7–36);
Lys$^{34}$(N$^\epsilon$-(7-deoxycholoyl))-GLP-1(7–36);
Lys$^{26,34}$-bis(N$^\epsilon$-(7-deoxycholoyl))-GLP-1(7–36);
Gly$^8$Lys$^{26}$(N$^\epsilon$-(7-deoxycholoyl))-GLP-1(7–36);
Gly$^8$Lys$^{34}$(N$^\epsilon$-(7-deoxycholoyl))-GLP-1(7–36);
Gly$^8$Lys$^{26,34}$-bis(N$^\epsilon$-(7-deoxycholoyl))-GLP-1(7–36);
Arg$^{26}$Lys$^{34}$(N$^\epsilon$-(7-deoxycholoyl))-GLP-1(7–36);
Lys$^{26}$(N$^\epsilon$-(7-deoxycholoyl))-GLP-1(7–35);
Lys$^{34}$(N$^\epsilon$-(7-deoxycholoyl))-GLP-1(7–35);
Lys$^{26,34}$-bis(N$^\epsilon$-(7-deoxycholoyl))-GLP-1(7–35);
Gly$^8$Lys$^{26}$(N$^\epsilon$-(7-deoxycholoyl))-GLP-1(7–35);
Gly$^8$Lys$^{34}$(N$^\epsilon$-(7-deoxycholoyl))-GLP-1(7–35);
Gly$^8$Lys$^{26,34}$-bis(N$^\epsilon$-(7-deoxycholoyl))-GLP-1(7–35);
Arg$^{26}$Lys$^{34}$(N$^\epsilon$-(7-deoxycholoyl))-GLP-1(7–35);
Lys$^{26}$(N$^\epsilon$-(7-deoxycholoyl))-GLP-1(7–36)amide;
Lys$^{34}$(N$^\epsilon$-(7-deoxycholoyl))-GLP-1(7–36)amide;
Lys$^{26,34}$-bis(N$^\epsilon$-(7-deoxycholoyl))-GLP-1(7–36)amide;
Gly$^8$Lys$^{26}$(N$^\epsilon$-(7-deoxycholoyl))-GLP-1(7–36)amide;
Gly$^8$Lys$^{34}$(N$^\epsilon$-(7-deoxycholoyl))-GLP-1(7–36)amide;
Gly$^8$Lys$^{26,34}$-bis(N$^\epsilon$-(7-deoxycholoyl))-GLP-1(7–36) amide;
Arg$^{26}$Lys$^{34}$(N$^\epsilon$-(7-deoxycholoyl))-GLP-1(7–36)amide;
Gly$^8$Arg$^{26}$Lys$^{34}$(N$^\epsilon$-(7-deoxycholoyl))-GLP-1(7–37);
Lys$^{26}$(N$^\epsilon$-(7-deoxycholoyl))Arg$^{34}$-GLP-1(7–37);
Gly$^8$Lys$^{26}$(N$^\epsilon$-(7-deoxycholoyl))Arg$^{34}$-GLP-1(7–37);
Arg$^{26,34}$Lys$^{36}$(N$^\epsilon$-(7-deoxycholoyl))-GLP-1(7–37);
Gly$^8$Arg$^{26,34}$Lys$^{36}$(N$^\epsilon$-(7-deoxycholoyl))-GLP-1(7–37);
Lys$^{26}$(N$^\epsilon$-(choloyl))-GLP-1(7–37);
Lys$^{34}$(N$^\epsilon$-(choloyl))-GLP-1(7–37);
Lys$^{26,34}$-bis(N$^\epsilon$-(choloyl))-GLP-1(7–37);
Gly$^8$Lys$^{26}$(N$^\epsilon$-(choloyl))-GLP-1(7–37);
Gly$^8$Lys$^{34}$(N$^\epsilon$-(choloyl))-GLP-1(7–37);
Gly$^8$Lys$^{26,34}$-bis(N$^\epsilon$-(choloyl))-GLP-1(7–37);
Arg$^{26}$Lys$^{34}$(N$^\epsilon$-(choloyl))-GLP-1(7–37);
Gly$^8$Arg$^{26}$Lys$^{34}$(N$^\epsilon$-(7-deoxycholoyl))-GLP-1(7–38);
Lys$^{26}$(N$^\epsilon$-(7-deoxycholoyl))Arg$^{34}$-GLP-1(7–38);
Gly$^8$Lys$^{26}$(N$^\epsilon$-(7-deoxycholoyl))Arg$^{34}$-GLP-1(7–38);
Arg$^{26,34}$Lys$^{36}$(N$^\epsilon$-(7-deoxycholoyl))-GLP-1(7–38);
Arg$^{26,34}$Lys$^{38}$(N$^\epsilon$-(7-deoxycholoyl))-GLP-1(7–38);
Gly$^8$Arg$^{26,34}$Lys$^{36}$(N$^\epsilon$-(7-deoxycholoyl))-GLP-1(7–38);
Lys$^{26}$(N$^\epsilon$-(choloyl))-GLP-1(7–38);
Lys$^{34}$(N$^\epsilon$-(choloyl))-GLP-1(7–38);
Lys$^{26,34}$-bis(N$^\epsilon$-(choloyl))-GLP-1(7–38);
Gly$^8$Lys$^{26}$(N$^\epsilon$-(choloyl))-GLP-1(7–38);
Gly$^8$Lys$^{34}$(N$^\epsilon$-(choloyl))-GLP-1(7–38);
Gly$^8$Lys$^{26,34}$-bis(N$^\epsilon$-(choloyl))-GLP-1(7–38);
Arg$^{26}$Lys$^{34}$(N$^\epsilon$-(choloyl))-GLP-1(7–38);
Gly$^8$Arg$^{26}$Lys$^{34}$(N$^\epsilon$-(7-deoxycholoyl))-GLP-1(7–39);
Lys$^{26}$(N$^\epsilon$-(7-deoxycholoyl))Arg$^{34}$-GLP-1(7–39);
Gly$^8$Lys$^{26}$(N$^\epsilon$-(7-deoxycholoyl))Arg$^{34}$-GLP-1(7–39);
Arg$^{26,34}$Lys$^{36}$(N$^\epsilon$-(7-deoxycholoyl))-GLP-1(7–39);
Gly$^8$Arg$^{26,34}$Lys$^{36}$(N$^\epsilon$-(7-deoxycholoyl))-GLP-1(7–39);
Lys$^{26}$(N$^\epsilon$-(choloyl))-GLP-1(7–39);
Lys$^{34}$(N$^\epsilon$-(choloyl))-GLP-1(7–39);
Lys$^{26,34}$-bis(N$^\epsilon$-(choloyl))-GLP-1(7–39);
Gly$^8$Lys$^{26}$(N$^\epsilon$-(choloyl))-GLP-1(7–39);
Gly$^8$Lys$^{34}$(N$^\epsilon$-(choloyl))-GLP-1(7–39);
Gly$^8$Lys$^{26,34}$-bis(N$^\epsilon$-(choloyl))-GLP-1(7–39);
Arg$^{26}$Lys$^{34}$(N$^\epsilon$-(choloyl))-GLP-1(7–39);
Gly$^8$Arg$^{26}$Lys$^{34}$(N$^\epsilon$-(7-deoxycholoyl))-GLP-1(7–40);
Lys$^{26}$(N$^\epsilon$-(7-deoxycholoyl))Arg$^{34}$-GLP-1(7–40);
Gly$^8$Lys$^{26}$(N$^\epsilon$-(7-deoxycholoyl))Arg$^{34}$-GLP-1(7–40);
Arg$^{26,34}$Lys$^{36}$(N$^\epsilon$-(7-deoxycholoyl))-GLP-1(7–40);
Gly$^8$Arg$^{26,34}$Lys$^{36}$(N$^\epsilon$-(7-deoxycholoyl))-GLP-1(7–40);
Lys$^{26}$(N$^\epsilon$-(choloyl))-GLP-1(7–40);
Lys$^{34}$(N$^\epsilon$-(choloyl))-GLP-1(7–40);
Lys$^{26,34}$-bis(N$^\epsilon$-(choloyl))-GLP-1(7–40);
Gly$^8$Lys$^{26}$(N$^\epsilon$-(choloyl))-GLP-1(7–40);
Gly$^8$Lys$^{34}$(N$^\epsilon$-(choloyl))-GLP-1(7–40);
Gly$^8$Lys$^{26,34}$-bis(N$^\epsilon$-(choloyl))-GLP-1(7–40);
Arg$^{26}$Lys$^{34}$(N$^\epsilon$-(choloyl))-GLP-1(7–40);
Lys$^{26}$(N$^\epsilon$-(choloyl))-GLP-1(7–36);
Lys$^{34}$(N$^\epsilon$-(choloyl))-GLP-1(7–36);
Lys$^{26,34}$-bis(N$^\epsilon$-(choloyl))-GLP-1(7–36);
Gly$^8$Lys$^{26}$(N$^\epsilon$-(choloyl))-GLP-1(7–36);

Gly⁸Lys³⁴(Nᵋ-(choloyl))-GLP-1(7–36);
Gly⁸Lys²⁶,³⁴-bis(Nᵋ-(choloyl))-GLP-1(7–36);
Arg²⁶Lys³⁴(Nᵋ-(choloyl))-GLP-1(7–36);
Lys²⁶(Nᵋ-(choloyl))-GLP-1(7–35);
Lys³⁴(Nᵋ-(choloyl))-GLP-1(7–35);
Lys²⁶,³⁴-bis(Nᵋ-(choloyl))-GLP-1(7–35);
Gly⁸Lys²⁶(Nᵋ-(choloyl))-GLP-1(7–35);
Gly⁸Lys³⁴(Nᵋ-(choloyl))-GLP-1(7–35);
Gly⁸Lys²⁶,³⁴-bis(Nᵋ-(choloyl))-GLP-1(7–35);
Arg²⁶Lys³⁴(Nᵋ-(choloyl))-GLP-1(7–35);
Lys²⁶(Nᵋ-(choloyl))-GLP-1(7–36)amide;
Lys³⁴(Nᵋ-(choloyl))-GLP-1(7–36)amide;
Lys²⁶,³⁴-bis(Nᵋ-(choloyl))-GLP-1(7–36)amide;
Gly⁸Lys²⁶(Nᵋ-(choloyl))-GLP-1(7–36)amide;
Gly⁸Lys³⁴(Nᵋ-(choloyl))-GLP-1(7–36)amide;
Gly⁸Lys²⁶,³⁴-bis(Nᵋ-(choloyl))-GLP-1(7–36)amide;
Arg²⁶Lys³⁴(Nᵋ-(choloyl))-GLP-1(7–36)amide;
Gly⁸Arg²⁶Lys³⁴(Nᵋ-(choloyl))-GLP-1(7–37);
Lys²⁶(Nᵋ-(choloyl))Arg³⁴-GLP-1(7–37);
Gly⁸Lys²⁶(Nᵋ-(choloyl))Arg³⁴-GLP-1(7–37);
Arg²⁶,³⁴Lys³⁶(Nᵋ-(choloyl))-GLP-1(7–37);
Gly⁸Arg²⁶,³⁴Lys³⁶(Nᵋ-(choloyl))-GLP-1(7–37);
Lys²⁶(Nᵋ-(lithocholoyl))-GLP-1(7–37);
Lys³⁴(Nᵋ-(lithocholoyl))-GLP-1(7–37);
Lys²⁶,³⁴-bis(Nᵋ-(lithocholoyl))-GLP-1(7–37);
Gly⁸Lys²⁶(Nᵋ-(lithocholoyl))-GLP-1(7–37);
Gly⁸Lys³⁴(Nᵋ-(lithocholoyl))-GLP-1(7–37);
Gly⁸Lys²⁶,³⁴-bis(Nᵋ-(lithocholoyl))-GLP-1(7–37);
Arg²⁶Lys³⁴(Nᵋ-(lithocholoyl))-GLP-1(7–37);
Gly⁸Arg²⁶Lys³⁴(Nᵋ-(choloyl))-GLP-1(7–38);
Lys²⁶(Nᵋ-(choloyl))Arg³⁴-GLP-1(7–38);
Gly⁸Lys²⁶(Nᵋ-(choloyl))Arg³⁴-GLP-1(7–38);
Arg²⁶,³⁴Lys³⁶(Nᵋ-(choloyl))-GLP-1(7–38);
Arg²⁶,³⁴Lys³⁸(Nᵋ-(choloyl))-GLP-1(7–38);
Gly⁸Arg²⁶,³⁴Lys³⁶(Nᵋ-(choloyl))-GLP-1(7–38);
Lys²⁶(Nᵋ-(lithocholoyl))-GLP-1(7–38);
Lys³⁴(Nᵋ-(lithocholoyl))-GLP-1(7–38);
Lys²⁶,³⁴-bis(Nᵋ-(lithocholoyl))-GLP-1(7–38);
Gly⁸Lys²⁶(Nᵋ-(lithocholoyl))-GLP-1(7–38);
Gly⁸Lys³⁴(Nᵋ-(lithocholoyl))-GLP-1(7–38);
Gly⁸Lys²⁶,³⁴-bis(Nᵋ-(lithocholoyl))-GLP-1(7–38);
Arg²⁶Lys³⁴(Nᵋ-(lithocholoyl))-GLP-1(7–38);
Gly⁸Arg²⁶Lys³⁴(Nᵋ-(choloyl))-GLP-1(7–39);
Lys²⁶(Nᵋ-(choloyl))Arg³⁴-GLP-1(7–39);
Gly⁸Lys²⁶(Nᵋ-(choloyl))Arg³⁴-GLP-1(7–39);
Arg²⁶,³⁴Lys³⁶(Nᵋ-(choloyl))-GLP-1(7–39);
Gly⁸Arg²⁶,³⁴Lys³⁶(Nᵋ-(choloyl))-GLP-1(7–39);
Lys²⁶(Nᵋ-(lithocholoyl))-GLP-1(7–39);
Lys³⁴(Nᵋ-(lithocholoyl))-GLP-1(7–39);
Lys²⁶,³⁴-bis(Nᵋ-(lithocholoyl))-GLP-1(7–39);
Gly⁸Lys²⁶(Nᵋ-(lithocholoyl))-GLP-1(7–39);
Gly⁸Lys³⁴(Nᵋ-(lithocholoyl))-GLP-1(7–39);
Gly⁸Lys²⁶,³⁴-bis(Nᵋ-(lithocholoyl))-GLP-1(7–39);
Arg²⁶Lys³⁴(Nᵋ-(lithocholoyl))-GLP-1(7–39);
Gly⁸Arg²⁶Lys³⁴(Nᵋ-(choloyl))-GLP-1(7–40);
Lys²⁶(Nᵋ-(choloyl))Arg³⁴-GLP-1(7–40);
Gly⁸Lys²⁶(Nᵋ-(choloyl))Arg³⁴-GLP-1(7–40);
Arg²⁶,³⁴Lys³⁶(Nᵋ-(choloyl))-GLP-1(7–40);
Gly⁸Arg²⁶,³⁴Lys³⁶(Nᵋ-(choloyl))-GLP-1(7–40);
Lys²⁶(Nᵋ-(lithocholoyl))-GLP-1(7–40);
Lys³⁴(Nᵋ-(lithocholoyl))-GLP-1(7–40);
Lys²⁶,³⁴-bis(Nᵋ-(lithocholoyl))-GLP-1(7–40);
Gly⁸Lys²⁶(Nᵋ-(lithocholoyl))-GLP-1(7–40);
Gly⁸Lys³⁴(Nᵋ-(lithocholoyl))-GLP-1(7–40);
Gly⁸Lys²⁶,³⁴-bis(Nᵋ-(lithocholoyl))-GLP-1(7–40);
Arg²⁶Lys³⁴(Nᵋ-(lithocholoyl))-GLP-1(7–37);
Lys²⁶(Nᵋ-(lithocholoyl))-GLP-1(7–36);
Lys³⁴(Nᵋ-(lithocholoyl))-GLP-1(7–36);
Lys²⁶,³⁴-bis(Nᵋ-(lithocholoyl))-GLP-1(7–36);
Gly⁸Lys²⁶(Nᵋ-(lithocholoyl))-GLP-1(7–36);
Gly⁸Lys³⁴(Nᵋ-(lithocholoyl))-GLP-1(7–36);
Gly⁸Lys²⁶,³⁴-bis(Nᵋ-(lithocholoyl))-GLP-1(7–36);
Arg²⁶Lys³⁴(Nᵋ-(lithocholoyl))-GLP-1(7–36);
Lys²⁶(Nᵋ-(lithocholoyl))-GLP-1(7–35);
Lys³⁴(Nᵋ-(lithocholoyl))-GLP-1(7–35);
Lys²⁶,³⁴-bis(Nᵋ-(lithocholoyl))-GLP-1(7–35);
Gly⁸Lys²⁶(Nᵋ-(lithocholoyl))-GLP-1(7–35);
Gly⁸Lys³⁴(Nᵋ-(lithocholoyl))-GLP-1(7–35);
Gly⁸Lys²⁶,³⁴-bis(Nᵋ-(lithocholoyl))-GLP-1(7–35);
Arg²⁶Lys³⁴(Nᵋ-(lithocholoyl))-GLP-1(7–35);
Lys²⁶(Nᵋ-(lithocholoyl))-GLP-1(7–36)amide;
Lys³⁴(Nᵋ-(lithocholoyl))-GLP-1(7–36)amide;
Lys²⁶,³⁴-bis(Nᵋ-(lithocholoyl))-GLP-1(7–36)amide;
Gly⁸Lys²⁶(Nᵋ-(lithocholoyl))-GLP-1(7–36)amide;
Gly⁸Lys³⁴(Nᵋ-(lithocholoyl))-GLP-1(7–36)amide;
Gly⁸Lys²⁶,³⁴-bis(Nᵋ-(lithocholoyl))-GLP-1(7–36)amide;
Arg²⁶Lys³⁴(Nᵋ-(lithocholoyl))-GLP-1(7–36)amide;
Gly⁸Arg²⁶Lys³⁴(Nᵋ-(lithocholoyl))-GLP-1(7–37);
Lys²⁶(Nᵋ-(lithocholoyl))Arg³⁴-GLP-1(7–37);
Gly⁸Lys²⁶(Nᵋ-(lithocholoyl))Arg³⁴-GLP-1(7–37);
Arg²⁶,³⁴Lys³⁶(Nᵋ-(lithocholoyl))-GLP-1(7–37);
Arg²⁶,³⁴Lys³⁸(Nᵋ-(lithocholoyl))-GLP-1(7–37);
Gly⁸Arg²⁶,³⁴Lys³⁶(Nᵋ-(lithocholoyl))-GLP-1(7–37);
Gly⁸Arg²⁶Lys³⁴(Nᵋ-(lithocholoyl))-GLP-1(7–38);
Lys²⁶(Nᵋ-(lithocholoyl))Arg³⁴-GLP-1(7–38);
Gly⁸Lys²⁶(Nᵋ-(lithocholoyl))Arg³⁴-GLP-1(7–38);
Arg²⁶,³⁴Lys³⁶(Nᵋ-(lithocholoyl))-GLP-1(7–38);
Arg²⁶,³⁴Lys³⁸(Nᵋ-(lithocholoyl))-GLP-1(7–38);
Gly⁸Arg²⁶,³⁴Lys³⁶(Nᵋ-(lithocholoyl))-GLP-1(7–38);
Gly⁸Arg²⁶Lys³⁴(Nᵋ-(lithocholoyl))-GLP-1(7–39);
Lys²⁶(Nᵋ-(lithocholoyl))Arg³⁴-GLP-1(7–39);
Gly⁸Lys²⁶(Nᵋ-(lithocholoyl))Arg³⁴-GLP-1(7–39);
Arg²⁶,³⁴Lys³⁶(Nᵋ-(lithocholoyl))-GLP-1(7–39);
Gly⁸Arg²⁶,³⁴Lys³⁶(Nᵋ-(lithocholoyl))-GLP-1(7–39);
Gly⁸Arg²⁶Lys³⁴(Nᵋ-(lithocholoyl))-GLP-1(7–40);
Lys²⁶(Nᵋ-(lithocholoyl))Arg³⁴-GLP-1(7–40);
Gly⁸Lys²⁶(Nᵋ-(lithocholoyl))Arg³⁴-GLP-1(7–40);
Arg²⁶,³⁴Lys³⁶(Nᵋ-(lithocholoyl))-GLP-1(7–40) and
Gly⁸Arg²⁶,³⁴Lys³⁶(Nᵋ-(lithocholoyl))-GLP-1(7–40).

In a further preferred embodiment, the present invention relates to a pharmaceutical composition comprising a GLP-1 derivative and a pharmaceutically acceptable vehicle or carrier.

In a further preferred embodiment, the present invention relates to the use of a GLP-1 derivative according to the invention for the preparation of a medicament which has a protracted profile of action relative to GLP-1(7–37).

In a further preferred embodiment, the present invention relates to the use of a GLP-1 derivative according to the invention for the preparation of a medicament with protracted effect for the treatment of non-insulin dependent diabetes mellitus.

In a further preferred embodiment, the present invention relates to the use of a GLP-1 derivative according to the invention for the preparation of a medicament with protracted effect for the treatment of insulin dependent diabetes mellitus.

In a further preferred embodiment, the present invention relates to the use of a GLP-1 derivative according to the invention for the preparation of a medicament with protracted effect for the treatment of obesity.

In a further preferred embodiment, the present invention relates to a method of treating insulin dependent or non-insulin dependent diabetes mellitus in a patient in need of such a treatment, comprising administering to the patient a therapeutically effective amount of a GLP-1 derivative of the invention, in particular a derivative of GLP-1(7-C), wherein C is 35 or 36, together with a pharmaceutically acceptable carrier.

According to U.S. Pat. No. 5,631,224 (Novo Nordisk A/S) a strong synergistic effect is observed in NIDDM patients by the combined treatment with GLP-1(7–37) or GLP-1(7–36) amide and an oral hypoglycemic agent.

Since pharmacodynamic and pharmacokinetic properties can be changed according to patients' demand by selecting a GLP-1 derivative of the present invention, additional therapeutic advantages can be gained by treating the NIDDM patients in a regimen which additionally comprises treatment with another antidiabetic agent.

Thus, the invention furthermore relates to the use of a GLP-1 derivative according to the present invention for the preparation of a medicament for use in the treatment of diabetes in a regimen which additionally comprises treatment with another antidiabetic agent.

In the present context the expression "antidiabetic agent" includes compounds for the treatment and/or prophylaxis of insulin resistance and diseases wherein insulin resistance is the pathophysiological mechanism.

In one embodiment of this invention, the antidiabetic agent is insulin or an analogue an a derivative thereof.

In another embodiment the antidiabetic agent is a hypoglycaemic agent, preferably an oral hypoglycaemic agent.

Oral hypoglycaemic agents are preferably selected from the group consisting of sulfonylureas, biguanides, thiazolidinediones, glucosidase inhibitors, glucagon antagonists, GLP-1 agonists, potassium channel openers, insulin sensitizers, hepatic enzyme inhibitors, glucose uptake modulators, compounds modifying the lipid metabolism, compounds lowering food intake, and agents acting on the ATP-dependent potassium channel of the β-cells.

Among the sulfonylureas, tolbutamide, glibenclamide, glipizide and gliclazide are preferred.

Among the biguanides, metformin is preferred.

Among the thiazolidinediones, troglitazone and ciglitazone are preferred.

Among the glucosidase inhibitors, acarbose is preferred.

Among the agents acting on the ATP-dependent potassium channel of the β-cells the following are preferred: glibenclamide, glipizide, gliclazide, repaglinide.

U.S. Pat. No. 5,424,286 describes a method for stimulating insulin release with exendin polypeptide(s). The Exendin polypeptides disclosed include HGEGTFTSDL-SKQMEEEAVRLFIEWLKNGGX (SEQ ID NO:1); wherein X=P or Y, and HX1X2GTFITSDLSKQMEEEAVRLFIEWLKNGGPSSGAPPPS (SEQ ID NO:2); wherein X1X2=SD (exendin-3) or GE (exendin-4). Accordingly to this document the insulinotropic effect of these polypeptides is greater than that attainable by administration of GLP-1.

The exendin-3 and -4 and fragments are useful in treatment of diabetes mellitus (types I or II) and prevention of hyperglycaemia. They normalise hyperglycaemia through glucose-dependent, insulin-independent and insulin-dependent mechanisms. These insulinotropic peptides are more active than GLP-1. Exendin-4 is specific for exendin receptors, i.e. it does not interact with vasoactive intestinal peptide receptors.

WO 9746584 describes truncated versions of exendin peptide(s) for treating diabetes. The disclosed peptides increase secretion and biosynthesis of insulin, but reduce those of glucagon. The truncated peptides can be made more economically than full length versions. Compared with GLP-1 and the known exendins, they are more active (effective at lower doses), more stable to degradation and metabolism and have a longer lasting effect.

However, the high clearance limits the usefulness of these compounds, and thus there still is a need for improvements in this field. Accordingly, it is one object of the present invention to provide derivatives of exendin and analogues thereof which have a protracted profile of action relative to native exendin.

Thus, in one aspect the invention relates to an exendin derivative wherein at least one amino acid residue of the parent peptide has a lipophilic substituent attached.

In a preferred embodiment only one lipophilic substituent is present.

In another preferred embodiment, the lipophilic substituent is attached to the N-terminal amino acid residue.

In another preferred embodiment, the lipophilic substituent is attached to the C-terminal amino acid residue.

In another preferred embodiment, the lipophilic substituent is attached to an amino acid residue which is not the N-terminal or C-terminal amino acid residue.

In further preferred embodiment, two lipophilic substituents are present.

In another preferred embodiment, one of the lipophilic substituents is attached to the N-terminal amino acid residue while the other is attached to the C-terminal amino acid residue.

In another preferred embodiment, one of the lipophilic substituents is attached to the C-terminal amino acid residue while the other is attached to an amino acid residue which is not the N-terminal or C-terminal amino acid residue.

In another preferred embodiment, both lipophilic substituents are attached to amino acid residues which are neither the N-terminal nor the C-terminal amino acid residue.

In further preferred embodiment, the lipophilic substituent comprises from 4 to 40 carbon atoms, more preferred from 8 to 25 carbon atoms, such as 12 to 18 carbon atoms.

In another preferred embodiment, a lipophilic substituent is attached to an amino acid residue in such a way that a carboxyl group of the lipophilic substituent forms an amide bond with an amino group of the amino acid residue.

In another preferred embodiment, a lipophilic substituent is attached to an amino acid residue in such a way that an amino group of the lipophilic substituent forms an amide bond with a carboxyl group of the amino acid residue.

In another preferred embodiment, the lipophilic substituent is attached to the parent peptide by means of a spacer.

In another preferred embodiment, the spacer is an unbranched alkane α,ω-dicarboxylic acid group having from 1 to 7 methylene groups, preferably two methylene groups, which form a bridge between an amino group of the parent peptide and an amino group of the lipophilic substituent.

In another preferred embodiment, the spacer is an amino acid residue except cys, or a dipeptide such as gly-lys.

In another preferred embodiment, a carboxyl group of the parent peptide forms an amide bond with an amino group of lys or a dipeptide containing a lys residue, and the other amino group of the lys spacer or a dipeptide spacer containing a lys residue forms an amide bond with a carboxyl group of the lipophilic substituent.

In another preferred embodiment, an amino group of the parent peptide forms an amide bond with a carboxylic group of the amino acid residue or dipeptide spacer, and an amino group of the amino acid residue or dipeptide spacer forms an amide bond with a carboxyl group of the lipophilic substituent.

In another preferred embodiment, a carboxyl group of the parent peptide forms an amide bond with an amino group of the amino acid residue spacer or dipeptide spacer, and a carboxyl group of the amino acid residue spacer or dipeptide spacer forms an amide bond with an amino group of the lipophilic substituent.

In another preferred embodiment, a carboxyl group of the parent peptide forms an amide bond with an amino group of a spacer which is asp or glu, or a dipeptide spacer containing a asp or glu residue, and a carboxyl group of the spacer forms an amide bond with an amino group of the lipophilic substituent.

In one embodiment said spacer is γ-aminobutyroyl.

In a further preferred embodiment, the lipophilic substituent comprises a partially or completely hydrogenated cyclopentanophenathrene skeleton.

In another preferred embodiment, the lipophilic substituent is an straight-chain or branched alkyl group.

In another preferred embodiment, the lipophilic substituent is the acyl group of a straight-chain or branched fatty acid.

In another preferred embodiment, the acyl group is selected from the group comprising $CH_3(CH_2)_nCO—$, wherein n is 4 to 38, preferably $CH_3(CH_2)_6CO—$, $CH_3(CH_2)_8CO—$, $CH_3(CH_2)_{10}CO—$, $CH_3(CH_2)_{12}CO—$, $CH_3(CH_2)_{14}CO—$, $CH_3(CH_2)_{16}CO—$, $CH_3(CH_2)_{18}CO—$, $CH_3(CH_2)_{20}CO—$ and $CH_3(CH_2)_{22}CO—$, most preferably hexadecanoyl.

In another preferred embodiment, the lipophilic substituent is an acyl group of a straight-chain or branched alkane α,ω-dicarboxylic acid.

In another preferred embodiment, the acyl group is selected from the group comprising $HOOC(CH_2)_mCO—$, wherein m is from 4 to 38, preferably from 4 to 24, more preferred selected from the group comprising $HOOC(CH_2)_{14}CO—$, $HOOC(CH_2)_{16}CO—$, $HOOC(CH_2)_{18}CO—$, $HOOC(CH_2)_{20}CO—$ and $HOOC(CH_2)_{22}CO—$.

In another preferred embodiment, the lipophilic substituent is a group of the formula $CH_3(CH_2)_p((CH_2)_qCOOH)CHNH—CO(CH_2)_2CO—$, wherein p and q are integers and p+q is an integer of from 8 to 33, preferably from 12 to 28.

In another preferred embodiment, the lipophilic substituent is a group of the formula $CH_3(CH_2)_rCO—NHCH(COOH)(CH_2)_2CO—$, wherein r is an integer of from 10 to 24.

In another preferred embodiment, the lipophilic substituent is a group of the formula $CH_3(CH_2)_sCO—NHCH((CH_2)_2 COOH)CO—$, wherein s is an integer of from 8 to 24.

In another preferred embodiment, the lipophilic substituent is a group of the formula $—NHCH(COOH)(CH_2)_4NH—CO(CH_2)_uCH_3$, wherein u is an integer of from 8 to 18.

In another preferred embodiment, the lipophilic substituent is a group of the formula $—NHCH(COOH)(CH_2)_4NH—COCH((CH_2)_2COOH)NH—CO(CH_2)_wCH_3$, wherein w is an integer of from 10 to 16.

In another preferred embodiment, the lipophilic substituent is a group of the formula $—NHCH(COOH)(CH_2)_4NH—CO(CH_2)_2CH(COOH)NH—CO(CH_2)_xCH_3$, wherein x is an integer of from 10 to 16.

In another preferred embodiment, the lipophilic substituent is a group of the formula $—NHCH(COOH)(CH_2)_4NH—CO(CH_2)_2CH(COOH)NH—CO(CH_2)_yCH_3$, wherein y is zero or an integer of from 1 to 22.

In another preferred embodiment, the designation analogue comprises derivatives wherein a total of up to fifteen, preferably up to ten amino acid residues have been exchanged with any α-amino acid residue.

In another preferred embodiment, the designation analogue comprises derivatives wherein a total of up to fifteen, preferably up to ten amino acid residues have been exchanged with any α-amino acid residue which can be coded for by the genetic code.

In another preferred embodiment, the designation analogue comprises derivatives wherein a total of up to six amino acid residues have been exchanged with any α-amino acid residue which can be coded for by the genetic code.

In another preferred embodiment, the parent peptide is HGEGTFTSDLSKQMEEEAVRLFIEWLKNGGX (SEQ ID NO:1), wherein X=P or Y, or a fragment or an analogue thereof.

In another preferred embodiment, the parent peptide is HX1X2GTFITSDLSKQMEEEAVRLFIEWLKNGGPSSG APPPS (SEQ ID NO:2), wherein X1X2=SD or GE, or a fragment or an analogue thereof.

In another preferred embodiment, the parent peptide is DLSKQMEEEAVRLFIEWLKNGGPSSGAPPPS (SEQ ID NO:3), or a fragment or an analogue thereof.

In another preferred embodiment the exendin derivative is selected from $Arg^{18}$, $Leu^{20}$, $Gln^{34}$, $Lys^{33}$ ($N^\epsilon$-(γ-aminobutyroyl($N^\alpha$-hexadecanoyl))) Exendin-4-(7–45)-$NH_2$, $Arg^{33}$, $Leu^{20}$, $Gln^{34}$, $Lys^{18}$ ($N^\epsilon$-(γ-aminobutyroyl($N^\alpha$-hexadecanoyl))) Exendin-4-(7–45)-$NH_2$.

The present invention furthermore relates to a pharmaceutical composition comprising an exendin derivative according to the present invention and a pharmaceutically acceptable vehicle or carrier.

Moreover, the invention is concerned with the use of an exendin derivative according to the present invention for the preparation of a medicament which has a protracted profile of action relative to exendin.

The invention also relates to the use of an exendin derivative according to the present invention for the preparation of a medicament with a protracted profile of action for the treatment of non-insulin dependent diabetes mellitus or for the treatment of insulin dependent diabetes mellitus or for the treatment of obesity.

The invention also relates to a method of treating insulin dependent or non-insulin dependent diabetes mellitus in a patient in need of such a treatment, comprising administering to the patient a therapeutically effective amount of a exendin derivative according to the present invention together with a pharmaceutically acceptable carrier.

DETAILED DESCRIPTION OF THE INVENTION

To obtain a satisfactory protracted profile of action of the GLP-1 derivative, the lipophilic substituent attached to the GLP-1 moiety preferably comprises 4–40 carbon atoms, in particular 8–25 carbon atoms. The lipophilic substituent may be attached to an amino group of the GLP-1 moiety by means of a carboxyl group of the lipophilic substituent which forms an amide bond with an amino group of the amino acid residue to which it is attached. Alternatively, the lipophilic substituent may be attached to said amino acid residue in such a way that an amino group of the lipophilic substituent forms an amide bond with a carboxyl group of the amino acid residue. As a further option, the lipophilic substituent may be linked to the GLP-1 moiety via an ester bond. Formally, the ester can be formed either by reaction between a carboxyl group of the GLP-1 moiety and a hydroxyl group of the substituent-to-be or by reaction between a hydroxyl group of the GLP-1 moiety and a carboxyl group of the substituent-to-be. As a further alternative, the lipophilic substituent can be an alkyl group which is introduced into a primary amino group of the GLP-1 moiety.

In one preferred embodiment of the invention, the lipophilic substituent is attached to the GLP-1 moiety by means of a spacer in such a way that a carboxyl group of the spacer forms an amide bond with an amino group of the GLP-1 moiety. Examples of suitable spacers are succinic acid, Lys, Glu or Asp, or a dipeptide such as Gly-Lys. When the spacer is succinic acid, one carboxyl group thereof may form an amide bond with an amino group of the amino acid residue, and the other carboxyl group thereof may form an amide bond with an amino group of the lipophilic substituent. When the spacer is Lys, Glu or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the $\epsilon$-amino group of Lys and the lipophilic substituent. In one preferred embodiment, such a further spacer is succinic acid which forms an amide bond with the $\epsilon$-amino group of Lys and with an amino group present in the lipophilic substituent. In another preferred embodiment such a further spacer is Glu or Asp which forms an amide bond with the $\epsilon$-amino group of Lys and another amide bond with a carboxyl group present in the lipophilic substituent, that is, the lipophilic substituent is a $N^\epsilon$-acylated lysine residue.

In another preferred embodiment of the present invention, the lipophilic substituent has a group which can be negatively charged. One preferred group which can be negatively charged is a carboxylic acid group.

The parent peptide can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, *Molecular Cloning: A Laboratory Manual,* Cold Spring Harbor Laboratory Press, New York, 1989). The DNA sequence encoding the peptide may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. The DNA sequence may also be prepared by polymerase chain reaction using specific primers, for instance as described in U.S. Pat. No. 4,683,202 or Saiki et al., *Science* 239 (1988), 487–491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replication in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are without limitation, *E. coli, Saccharomyces cerevisiae,* or mammalian BHK or CHO cell lines.

Examples of compounds which can be useful as GLP-1 moieties according to the present invention are described in International Patent Application No. WO 87/06941 (The General Hospital Corporation) which relates to a peptide fragment which comprises GLP-1(7–37) and functional derivatives thereof and to its use as an insulinotropic agent.

Further GLP-1 analogues are described in International Patent Application No. 90/11296 (The General Hospital Corporation) which relates to peptide fragments which comprise GLP-1(7–36) and functional derivatives thereof and have an insulinotropic activity which exceeds the insulinotropic activity of GLP-1(1–36) or GLP-1(1–37) and to their use as insulinotropic agents.

International Patent Application No. 91/11457 (Buckley et al.) discloses analogues of the active GLP-1 peptides 7–34, 7–35, 7–36, and 7–37 which can also be useful as GLP-1 moieties according to the present invention.

Pharmaceutical Compositions

Pharmaceutical compositions containing a GLP-1 derivative according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the GLP-1 derivative in the form of a nasal or pulmonal spray. As a still further option, the GLP-1 derivatives of the invention can also be administered transdermally, e.g. from a patch, optionally a iontophoretic patch, or transmucosally, e.g. bucally.

Pharmaceutical compositions containing a GLP-1 derivative of the present invention may be prepared by conventional techniques, e.g. as described in Remington's *Pharmaceutical Sciences,* 1985 or in Remington: *The Science and Practice of Pharmacy,* 19$^{th}$ edition, 1995.

Thus, the injectable compositions of the GLP-1 derivative of the invention can be prepared using the conventional techniques of the pharmaceutical industry which involves dissolving and mixing the ingredients as appropriate to give the desired end product.

According to one procedure, the GLP-1 derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hydroxybenzoate and benzyl alcohol.

Examples of suitable buffers are sodium acetate and sodium phosphate.

Further to the above-mentioned components, solutions containing a GLP-1 derivative according to the present invention may also contain a surfactant in order to improve the solubility and/or the stability of the GLP-1 derivative.

A composition for nasal administration of certain peptides may, for example, be prepared as described in European Patent No. 272097 (to Novo Nordisk A/S) or in WO 93/18785.

According to one preferred embodiment of the present invention, the GLP-1 derivative is provided in the form of a composition suitable for administration by injection. Such a composition can either be an injectable solution ready for use or it can be an amount of a solid composition, e.g. a lyophilised product, which has to be dissolved in a solvent before it can be injected. The injectable solution preferably contains not less than about 2 mg/ml, preferably not less than about 5 mg/ml, more preferred not less than about 10 mg/ml of the GLP-1 derivative and, preferably, not more than about 100 mg/ml of the GLP-1 derivative.

The GLP-1 derivatives of this invention can be used in the treatment of various diseases. The particular GLP-1 derivative to be used and the optimal dose level for any patient will depend on the disease to be treated and on a variety of factors including the efficacy of the specific peptide derivative employed, the age, body weight, physical activity, and diet of the patient, on a possible combination with other drugs, and on the severity of the case. It is recommended that the dosage of the GLP-1 derivative of this invention be determined for each individual patient by those skilled in the art.

In particular, it is envisaged that the GLP-1 derivative will be useful for the preparation of a medicament with a protracted profile of action for the treatment of non-insulin dependent diabetes mellitus and/or for the treatment of obesity.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

The following acronyms for commercially available chemicals are used:

| | |
|---|---|
| DMF: | N,N-Dimethylformamide. |
| DCC: | N,N-Dicyclohexylcarbodiimide |
| NMP: | N-Methyl-2-pyrrolidone. |
| EDPA: | N-Ethyl-N,N-diisopropylamine. |
| EGTA: | Ethylene glycol-bis(β-aminoethyl ether)-N,N,N',N'-tetraacetic acid. |
| GTP | Guanosine 5'-triphosphate. |
| TFA: | Trifluoroacetic acid. |
| THF: | Tetrahydrofuran |
| H-Glu(OH)-OBu$^t$: | L-Glutamic acid α-tert-butyl ester |
| Cap-ONSu: | Octanoic acid 2,5-dioxopyrrolidin-1-yl ester |
| Lau-ONSu: | Dodecanoic acid 2,5-dioxopyrrolidin-1-yl ester |
| Myr-ONSu: | Tetradecanoic acid 2,5-dioxopyrrolidin-1-yl ester. |
| Pal-ONSu: | Hexadecanoic acid 2,5-dioxopyrrolidin-1-yl ester. |
| Ste-ONSu: | Octadecanoic acid 2,5-dioxopyrrolidin-1-yl ester. |

Abbreviations

| | |
|---|---|
| PDMS: | Plasma Desorption Mass Spectrometry |
| MALDI-MS: | Matrix Assisted Laser Desorption/Ionisation Mass Spectrometry |
| HPLC: | High Performance Liquid Chromatography |
| amu: | atomic mass units |
| Lit-Glu(ONSu)-OBu$^t$: | N$^α$-Lithochoyl-L-glutamic-acid α-t-butyl ester γ-2,5-dioxopyrrolidin-1-yl ester |

-continued

| | |
|---|---|
| Cap-Glu(ONSu)-OBu$^t$: | N$^\alpha$-Octanoyl-L-glutamic acid α-t-butyl ester γ-2,5-dioxopyrrolidin-1-yl ester |
| Cac-Glu(ONSu)-OBu$^t$: | N$^\alpha$-Decanoyl-L-glutamic acid α-t-butyl ester γ-2,5-dioxopyrrolidin-1-yl ester |
| Lau-Glu(ONSu)-OBu$^t$: | N$^\alpha$-Dodecanoyl-L-glutamic acid α-t-butyl ester γ-2,5-dioxopyrrolidin-1-yl ester |
| Myr-Glu(ONSu)-OBu$^t$: | N$^\alpha$-Tetradecanoyl-L-glutamic acid α-t-butyl ester γ-2,5-dioxopyrrolidin-1-yl ester |
| Pal-Glu(ONSu)-OBu$^t$: | N$^\alpha$-Hexadecanoyl-(L)-glutamic acid α-t-butyl-γ-2,5-dioxopyrrolidin-1-yl-diester. |
| Ste-Glu(ONSu)-OBu$^t$: | N$^\alpha$-Octadecanoyl-(L)-glutamic acid α-t-butyl-γ-2,5-dioxopyrrolidin-1-yl diester |
| Lau-β-Ala-ONSu: | N$^\beta$-Dodecanoyl-β-alanine 2,5-dioxopyrrolidin-1-yl-ester |
| Pal-β-Ala-ONSu: | N$^\beta$-Hexadecanoyl-β-alanine 2,5-dioxopyrrolidin-1-yl ester |
| Lau-GABA-ONSu: | N$^\gamma$-Dodecanoyl-γ-aminobutyric acid 2,5-dioxopyrrolidin-1-yl ester |
| Myr-GABA-ONSu: | N$^\gamma$-Tetradecanoyl-γ-aminobutyric acid 2,5-dioxopyrrolidin-1-yl ester |
| Pal-GABA-ONSu: | N$^\gamma$-Hexadecanoyl-γ-aminobutyric acid 2,5-dioxopyrrolidin-1-yl ester |
| Ste-GABA-ONSu: | N$^\gamma$-Octadecanoyl-γ-aminobutyric acid 2,5-dioxopyrrolidin-1-yl ester |
| Pal-Isonip-ONSu: | N-Hexadecanoyl-piperidine-4-carboxylic acid 2,5-dioxopyrrolidin-1-yl ester |
| Pal-Glu(OBu$^t$)-ONSu: | N$^\alpha$-Hexadecanoyl-L-glutamic acid α-2,5-dioxopyrrolidin-1-yl ester γ-t-butyl ester |
| HOOC-(CH$_2$)$_6$-COONSu: | ω-Carboxyheptanoic acid 2,5-dioxopyrrolidin-1-yl ester. |
| HOOC-(CH$_2$)$_{10}$-COONSu: | ω-Carboxyundecanoic acid 2,5-dioxopyrrolidin-1-yl ester. |
| HOOC-(CH$_2$)$_{12}$-COONSu: | ω-Carboxytridecanoic acid 2,5-dioxopyrrolidin-1-yl ester. |
| HOOC-(CH$_2$)$_{14}$-COONSu: | ω-Carboxypentadecanoic acid 2,5-dioxopyrrolidin-1-yl ester. |
| HOOC-(CH$_2$)$_{16}$-COONSu: | ω-Carboxyheptadecanoic acid 2,5-dioxopyrrolidin-1-yl ester. |
| HOOC-(CH$_2$)$_{18}$-COONSu: | ω-Carboxynonadecanoic acid 2,5-dioxopyrrolidin-1-yl ester. |

Analytical

Plasma Desorption Mass Spectrometry

Sample Preparation:

The sample is dissolved in 0.1% TFA/EtOH (1:1) at a concentration of 1 μg/μl. The sample solution (5–10 μl) is placed on a nitrocellulose target (Bio-ion, AB, Uppsala, Sweden) and allowed to adsorb to the target surface for 2 minutes. The target is subsequently rinsed with 2×25 μl 0.1% TFA and spin-dried. Finally, the nitrocellulose target is placed in a target carrousel and introduced into the mass spectrometer.

MS Analysis:

PDMS analysis was carried out using a Bio-ion 20 time-of flight instrument (Bio-ion Nordic AB, Uppsala, Sweden). An acceleration voltage of 15 kV was applied and molecular ions formed by bombardment of the nitrocellulose surface with 252-Cf fission fragments were accelerated towards a stop detector. The resulting time-of-flight spectrum was calibrated into a true mass spectrum using the H$^+$ and NO$^+$ ions at m/z 1 and 30, respectively. Mass spectra were generally accumulated for $1.0 \times 10^6$ fission events corresponding to 15–20 minutes. Resulting assigned masses all correspond to isotopically averaged molecular masses. The accuracy of mass assignment is generally better than 0.1%.

MALDI-MS

MALDI-TOF MS analysis was carried out using a Voyager RP instrument (PerSeptive Biosystems Inc., Framingham, Mass) equipped with delayed extraction and operated in linear mode. Alpha-cyano-4-hydroxy-cinnamic acid was used as matrix, and mass assignments were based on external calibration.

Example 1

Synthesis of N$^\alpha$-hexadecanoyl-Glu(ONSu)-OBu$^t$

To a suspension of H-Glu(OH)-OBu$^t$ (4.2 g, 20.6 mmol), DMF (500 ml) and EDPA (2.65 g, 20.6 mmol) was added drop by drop a solution of Pal-ONSu (7.3 g, 20.6 mmol) in DMF (100 ml). The reaction mixture was stirred for 64 h at room temperature and then concentrated in vacuo to a total volume of 20 ml. The residue was partitioned between 10% aqueous citric acid (300 ml) and ethyl acetate (250 ml), and the phases were separated. The organic phase was concentrated in vacuo and the residue dissolved in DMF (50 ml). The resulting solution was added drop by drop to a 10% aqueous solution of citric acid (500 ml) kept at 0° C. The precipitated compound was collected and washed with iced water and dried in a vacuum drying oven. The dried compound was dissolved in DMF (45 ml) and HONSu (2.15 g, 18.7 mmol) was added. To the resulting mixture was added a solution of N,N'-dicyclohexylcarbodiimide (3.5 g, 17 mmol) in dichloromethane (67 ml). The reaction mixture was stirred for 16 h at room temperature, and the precipitated compound was filtered off. The precipitate was recrystallised from n-heptane/2-propanol to give the title compound (6.6 g, 72%).

Example 2

Synthesis of N$^\alpha$-octadecanoyl-Glu(ONSu)-OBu$^t$

To a suspension of H-Glu(OH)-OBu$^t$ (2.82 g, 13.9 mmol), DMF (370 ml) and EDPA (1.79 g, 13.9 mmol) was added drop by drop a solution of Ste-ONSu (5.3 g, 13.9 mmol) in DMF (60 ml). Dichloromethane (35 ml) was added, and the reaction mixture was stirred for 24 h at room temperature and then concentrated in vacuo. The residue was partitioned between 10% aqueous citric acid (330 ml) and ethyl acetate (200 ml), and the phases were separated. The organic phase was concentrated in vacuo and the residue dissolved in DMF (60 ml). The resulting solution was added drop by drop to a 10% aqueous solution of citric acid (400 ml) kept at 0° C. The precipitated compound was collected and washed with iced water and dried in a vacuum drying oven. The dried compound was dissolved in DMF (40 ml) and HONSu (1.63 g, 14.2 mmol) was added. To the resulting mixture was added a solution of DCC (2.66 g, 12.9 mmol) in dichloromethane (51 ml). The reaction mixture was stirred for 64 h at room temperature, and the precipitated compound was filtered off. The precipitate was recrystallised from n-heptane/2-propanol to give the title compound (4.96 g, 68%).

Example 3

Synthesis of Arg$^{26,34}$, Lys$^{36}$ (N$^\varepsilon$-(γ-glutamyl(N$^\alpha$-hexadecanoyl))) GLP-1 (7–36)-OH To a mixture of Arg$^{26,34}$, Lys$^{36}$ GLP-1 (7–36)-OH (12.2 mg, 3.67 μmol), EDPA (13.3 mg, 103 μmol), NMP (1.71 ml)

and water (855 μl) was added a solution of PaI-Glu(ONSu)-OBu$^t$ (5.94 mg, 11 μmol), prepared as described above, in NMP (148 μl). The reaction mixture was gently shaken for 5 min. at room temperature, and then allowed to stand for an additional 90 min. at room temperature. The reaction was quenched by the addition of a solution of glycine (6 mg, 81 μmol) in water (0.6 ml). A 0.5% aqueous solution of ammonium-acetate (38 ml) was added, and the resulting mixture eluted onto a Varian 5g C8 Mega Bond Elut®, the immobilised compound washed with 5% aqueous acetonitril (20 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0–100% in 60 minutes. The title compound (3.1 mg, 23%) was isolated, and the product was analysed by PDMS. The m/z value for the protonated molecular ion was found to be 3695±3. The resulting molecular weight is thus 3694±3 amu (theoretical value 3694 amu).

Example 4

Synthesis of $Arg^{26,34}$, $Lys^{36}$ ($N^\epsilon$-($\gamma$-glutamyl($N^\alpha$-octadecanoyl$))) GLP-1 (7–36)-OH To a mixture of $Arg^{26,34}$, $Lys^{36}$ GLP-1 (7–36)-OH (12.2 mg, 3.7 μmol), EDPA (13.3 mg, 103 μmol), NMP (1.71 ml) and water (855 μl) was added a solution of Ste-Glu(ONSu)-OBu$^t$ (6.25 mg, 11 μmol), prepared as above, in NMP (1 ml). The reaction mixture was gently shaken for 5 min. at room temperature, and then allowed to stand for an additional 90 min. at room temperature. The reaction was quenched by the addition of a solution of glycine (6 mg, 81 μmol) in water (0.6 ml). A 0.5% aqueous solution of ammonium acetate (54 ml) was added, and the resulting mixture eluted onto a Varian 5g C8 Mega Bond Elut®, the immobilised compound washed with 5% aqueous acetonitril (20 ml), and finally liberated from the cartridge by elution with TFA (25 ml). The eluate was concentrated in vacuo, and the residue purified by column chromatography using a cyanopropyl column (Zorbax 300SB-CN) and a standard acetonitril/TFA system. The column was heated to 65° C. and the acetonitril gradient was 0–100% in 60 minutes. The title compound (3.7 mg, 27%) was isolated, and the product was analysed by PDMS. The m/z value for the protonated molecular ion was found to be 3723±3. The resulting molecular weight is thus 3722±3 amu (theoretical value 3722 amu).

Example 5

Synthesis of $Arg^{18}$, $Leu^{20}$, $Gln^{34}$, $Lys^{33}$ ($N^\epsilon$-($\gamma$-aminobutyroyl($N^\alpha$-hexadecanoyl$))) Exendin-4-(7–45)-$NH_2$ To a mixture of $Arg^{18}$, $Leu^{20}$, $Gln^{34}$-Exendin-4-$NH_2$ (9.7 mg, 2.3 μmol), EDPA (8.4 mg, 64.7 μmol), NMP (1.36 ml) and water (0.68 ml) was added a solution of PaI-GABA-ONSu (3 mg, 6.9 μmol) in NMP (76 μl). The reaction mixture was gently shaken for 5 min., and then allowed to stand for an additional 90 min. at room temperature. The reaction was quenched by the addition of a solution of glycine (3.8 mg, 50.8 μmol) in water (38 μl). The resulting mixture was purified by column chromatography using a cyanopropyl column (Zorbax 300SB-CN) and a standard acetonitril/TFA system. The column was heated to 65° C. and the acetonitril gradient was 0–100% in 60 minutes. The title compound (4.5 mg, 43%) was isolated, and the product was analysed by PDMS. The m/z value for the protonated molecular ion was found to be 4532.8±3. The resulting molecular weight is thus 4531.8±3 amu (theoretical value 4534 amu).

Example 6

Synthesis of $Arg^{33}$, $Leu^{20}$, $Gln^{34}$, $Lys^{18}$ ($N^\epsilon$-($\gamma$-aminobutyroyl($N^\alpha$-hexadecanoyl$))) Exendin-4-(7–45)-$NH_2$ To a mixture of $Arg^{33}$, $Leu^{20}$, $Gln^{34}$-Exendin-4-$NH_2$ (10 mg, 2.4 μmol), EDPA (8.6 mg, 66.5 μmol), NMP (1.4 ml) and water (0.7 ml) was added a solution of PaI-GABA-ONSu (3.1 mg, 7.1 μmol) in NMP (78 μl). The reaction mixture was gently shaken for 5 min., and then allowed to stand for an additional 145 min. at room temperature. The reaction was quenched by the addition of a solution of glycine (3.9 mg, 52.3 μmol) in water (39 μl). The resulting mixture was purified by column chromatography using a cyanopropyl column (Zorbax 300SB-CN) and a standard acetonitril/TFA system. The column was heated to 65° C. and the acetonitril gradient was 0–100% in 60 minutes. The title compound (2.9 mg, 21%) was isolated, and the product was analysed by PDMS. The m/z value for the protonated molecular ion was found to be 4533.8±3. The resulting molecular weight is thus 4532.8±3 amu (theoretical value 4534 amu).

BIOLOGICAL FINDINGS

Protraction of GLP-1 Derivatives after s.c. Administration

The protraction of a number GLP-1 derivatives of the invention was determined by monitoring the concentration thereof in plasma after sc administration to healthy pigs, using the method described below. For comparison also the concentration in plasma of GLP-1(7–37) after sc. administration was followed. The protraction of other GLP-1 derivatives of the invention can be determined in the same way.

Pigs (50% Duroc, 25% Yorkshire, 25% Danish Landrace, app 40 kg) were fasted from the beginning of the experiment. To each pig 0.5 nmol of test compound per kg body weight was administered in a 50 μM isotonic solution (5 mM phosphate, pH 7.4, 0.02% Tween®-20 (Merck), 45 mg/ml mannitol (pyrogen free, Novo Nordisk). Blood samples were drawn from a catheter in vena jugularis. 5 ml of the blood samples were poured into chilled glasses containing 175 μl of the following solution: 0.18 M EDTA, 1500 KIE/ml aprotinin (Novo Nordisk) and 3% bacitracin (Sigma), pH 7.4. Within 30 min, the samples were centrifuged for 10 min at 5–6000*g. Temperature was kept at 4° C. The supernatant was pipetted into different glasses and kept at minus 20° C. until use.

The plasma concentrations of the peptides were determined by RIA using a monoclonal antibody specific for the N-terminal region of GLP-1(7–37). The cross reactivities were less than 1% with GLP-1(1–37) and GLP-1(8–36) amide and <0.1% with GLP-1(9–37), GLP-1(10–36)amide and GLP-1(11–36)amide. The entire procedure was carried out at 4° C.

The assay was carried out as follows: 100 μl plasma was mixed with 271 μl 96% ethanol, mixed using a vortex mixer and centrifuged at 2600*g for 30 min. The supernatant was decanted into Minisorp tubes and evaporated completely (Savant Speedvac AS290). The evaporation residue was reconstituted in the assay buffer consisting of 80 mM NaH$_2$PO$_4$/Na$_2$HPO$_4$, 0.1% HSA (Orpha 20/21, Behring), 10 mM EDTA, 0.6 mM thiomersal (Sigma), pH 7.5. Samples were reconstituted in volumes suitable for their expected concentrations, and were allowed to reconstitute for 30 min. To 300 µl sample, 100 µl antibody solution in dilution buffer containing 40 mM NaH$_2$PO$_4$/Na$_2$HPO$_4$, 0.1% HSA, 0.6 mM thiomersal, pH 7.5, was added. A non-specific sample was prepared by mixing 300 µl buffer with 100 µl dilution buffer. Individual standards were prepared from freeze dried stocks, dissolved in 300 µl assay buffer. All samples were pre-incubated in Minisorp tubes with antibody as described above for 72 h. 200 µl tracer in dilution buffer containing 6–7000 CPM was added, samples were mixed and incubated for 48 h. 1.5 ml of a suspension of 200 ml per liter of heparin-stabilised bovine plasma and 18 g per liter of activated carbon (Merck) in 40 mM NaH$_2$PO$_4$/Na$_2$HPO$_4$, 0.6 mM thiomersal, pH 7.5, was added to each tube. Before use, the suspension was mixed and allowed to stand for 2 h at 4° C. All samples were incubated for 1 h at 4° C. and then centrifuged at 3400*g for 25 min. Immediately after the centrifugation, the supernatant was decanted and counted in a γ-counter. The concentration in the samples was calculated from individual standard curves. Plasma concentrations were found, calculated as % of the maximum concentration for the individual compounds (n=2). The GLP-1 derivatives of the invention have a protracted profile of action relative to GLP-1(7–37) and are much more persistent in plasma than GLP-1(7–37). The time at which the peak concentration in plasma is achieved varies within wide limits, depending on the particular GLP-1 derivative selected.

Stimulation of cAMP Formation in a Cell Line Expressing the Cloned Human GLP-1 Receptor In order to demonstrate efficacy of the GLP-1 derivatives, their ability to stimulate formation of cAMP in a cell line expressing the cloned human GLP-1 receptor was tested. An EC$_{50}$ was calculated from the dose-response curve.

Baby hamster kidney (BHK) cells expressing the human pancreatic GLP-1 receptor were used (Knudsen and Pridal, 1996, Eur. J. Pharm. 318, 429–435). Plasma membranes were prepared (Adelhorst et al, 1994, J. Biol. Chem. 269, 6275) by homogenisation in buffer (10 mmol/l Tris-HCl and 30 mmol/l NaCl pH 7.4, containing, in addition, 1 mmol/l dithiothreitol, 5 mg/l leupeptin (Sigma, St. Louis, Mo., USA), 5 mg/l pepstatin (Sigma, St. Louis, Mo., USA), 100 mg/l bacitracin (Sigma, St. Louis, Mo., USA), and 16 mg/l aprotinin (Novo Nordisk A/S, Bagsvaerd, Denmark)). The homogenate was centrifuged on top of a layer of 41 w/v % sucrose. The white band between the two layers was diluted in buffer and centrifuged. Plasma membranes were stored at −80° C. until used.

The assay was carried out in 96-well microtiter plates in a total volume of 140 µl. The buffer used was 50 mmol/l Tris-HCl, pH 7.4 with the addition of 1 mmol/l EGTA, 1.5 mmol/l MgSO$_4$, 1.7 mmol/l ATP, 20 mM GTP, 2 mmol/l 3-isobutyl-1-methylxanthine, 0.01% Tween-20 and 0.1% human serum albumin (Reinst, Behringwerke AG, Marburg, Germany). Compounds to be tested for agonist activity were dissolved and diluted in buffer, added to the membrane preparation and the mixture was incubated for 2 h at 37° C. The reaction was stopped by the addition of 25 µl of 0.05 mol/l HCl. Samples were diluted 10 fold before analysis for cAMP by a scintillation proximity assay (RPA 538, Amersham, UK).

The invention claimed is:

1. A derivative of exendin-4 or a fragment thereof, wherein said derivative has one lipophilic substituent attached, optionally via a spacer, to an amino acid residue of said exendin-4 or fragment thereof, which is not the N-terminal or C-terminal amino acid residue of said exendin-4 or fragment thereof, wherein said fragment has insulinotropic activity.

2. A pharmaceutical composition comprising a derivative of claim 1 and a pharmaceutically acceptable vehicle or carrier.

3. A method of treating insulin dependent or non-insulin dependent diabetes mellitus in a patient in need of such a treatment, comprising administering to the patient a therapeutically effective amount of a derivative of claim 1 and a pharmaceutically acceptable carrier.

4. The derivative of claim 1, wherein the lipophilic substituent has 4 to 40 carbon atoms.

5. The derivative of claim 4, wherein the lipophilic substituent has 8 to 25 carbon atoms.

6. The derivative of claim 4, wherein the lipophilic substituent is attached by means of a spacer.

7. The derivative of claim 6, wherein the spacer is an unbranched alkane α,ω-dicarboxylic acid group having from 1 to 7 methylene groups.

8. The derivative of claim 4, wherein the lipophilic substituent is a straight-chain or branched acyl group.

9. The derivative of claim 8, wherein the acyl group is of the formula $CH_3(CH_2)_nCO-$, wherein n is 4 to 38.

10. The derivative of claim 9, wherein the acyl group is $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ or $CH_3(CH_2)_{22}CO-$.

* * * * *

UNITED STATES PATENT AND TRADEMARK OFFICE
CERTIFICATE OF CORRECTION

PATENT NO.        : 7,226,990 B2
APPLICATION NO. : 09/886311
DATED             : June 5, 2007
INVENTOR(S)       : Knudsen et al.

It is certified that error appears in the above-identified patent and that said Letters Patent is hereby corrected as shown below:

On the Title Page 1, at Item (60): Please replace the Provisional Application No. "60/084,351" with --60/084,357-- as it appears in the Declaration and Oath as filed.

Signed and Sealed this

Eleventh Day of December, 2007

JON W. DUDAS
*Director of the United States Patent and Trademark Office*